United States Patent
Roh et al.

(10) Patent No.: US 11,857,264 B2
(45) Date of Patent: *Jan. 2, 2024

(54) SYSTEMS AND METHODS FOR PHYSICIAN DESIGNED SURGICAL PROCEDURES

(71) Applicant: Carlsmed, Inc., Carlsbad, CA (US)

(72) Inventors: Jeffrey Roh, Seattle, WA (US); Justin Esterberg, Mercer Island, WA (US)

(73) Assignee: Carlsmed, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/899,370

(22) Filed: Aug. 30, 2022

(65) Prior Publication Data

US 2023/0000560 A1 Jan. 5, 2023

Related U.S. Application Data

(63) Continuation of application No. 17/702,591, filed on Mar. 23, 2022, now Pat. No. 11,497,559, which is a
(Continued)

(51) Int. Cl.
*A61B 34/10* (2016.01)
*A61B 34/20* (2016.01)
(Continued)

(52) U.S. Cl.
CPC .............. *A61B 34/10* (2016.02); *A61B 5/743* (2013.01); *A61B 5/748* (2013.01); *A61B 5/7435* (2013.01);
(Continued)

(58) Field of Classification Search
CPC ....... A61B 34/10; A61B 5/743; A61B 5/7435; A61B 5/748; A61B 34/20; A61B 34/25;
(Continued)

(56) References Cited

U.S. PATENT DOCUMENTS 4,704,686 A 11/1987 Aldinger
4,936,862 A 6/1990 Walker et al.
(Continued)

FOREIGN PATENT DOCUMENTS

CN 104318009 A 1/2015
CN 104353121 A 2/2015
(Continued)

OTHER PUBLICATIONS

Extended European Search Report for European Application No. 19890663.8, dated Jul. 29, 2022, 8 pages.
(Continued)

*Primary Examiner* — Jerome Grant, II
(74) *Attorney, Agent, or Firm* — Perkins Coie LLP

(57) ABSTRACT

Systems and methods for providing assistance to a surgeon during an implant surgery are disclosed. A method includes defining areas of interest in diagnostic data of a patient and defining a screw bone type based on the surgeon's input. Post defining the areas of interest, salient points are determined for the areas of interest. Successively, an XZ angle, an XY angle, and a position entry point for a screw are determined based on the salient points of the areas of interest. Successively, a maximum screw diameter and a length of the screw are determined based on the salient points. Thereafter, the screw is identified and suggested to the surgeon for usage during the implant surgery.

22 Claims, 12 Drawing Sheets

Related U.S. Application Data continuation of application No. 17/497,546, filed on Oct. 8, 2021, which is a continuation of application No. 16/048,167, filed on Jul. 27, 2018, now Pat. No. 11,166,764.

(60) Provisional application No. 62/537,869, filed on Jul. 27, 2017.

(51) Int. Cl.

| | | |
|---|---|---|
| *A61B 34/00* | (2016.01) | |
| *G06T 19/00* | (2011.01) | |
| *A61B 90/00* | (2016.01) | |
| *G16H 40/63* | (2018.01) | |
| *G06T 7/73* | (2017.01) | |
| *G16H 20/40* | (2018.01) | |
| *G16H 50/00* | (2018.01) | |
| *G06N 20/00* | (2019.01) | |
| *A61B 5/00* | (2006.01) | |
| *G06N 5/01* | (2023.01) | |

(52) U.S. Cl.
CPC .............. *A61B 34/20* (2016.02); *A61B 34/25* (2016.02); *A61B 90/37* (2016.02); *G06N 20/00* (2019.01); *G06T 7/73* (2017.01); *G06T 19/006* (2013.01); *G16H 20/40* (2018.01); *G16H 40/63* (2018.01); *G16H 50/00* (2018.01); *A61B 2034/102* (2016.02); *A61B 2034/105* (2016.02); *A61B 2034/107* (2016.02); *A61B 2034/108* (2016.02); *A61B 2034/256* (2016.02); *A61B 2090/365* (2016.02); *G06N 5/01* (2023.01); *G06T 2207/10072* (2013.01); *G06T 2207/10116* (2013.01); *G06T 2207/20084* (2013.01); *G06T 2207/30012* (2013.01)

(58) Field of Classification Search
CPC .............. A61B 90/37; A61B 2034/102; A61B 2034/105; A61B 2034/107; A61B 2034/108; A61B 2034/256; A61B 2090/365; G06N 20/00; G06N 5/01; G06T 7/73; G06T 19/006; G06T 2207/10072; G06T 2207/10116; G06T 2207/20084; G06T 2207/30012; G16H 20/40; G16H 40/63; G16H 50/00
USPC .......................................................... 382/128
See application file for complete search history.

(56) References Cited

U.S. PATENT DOCUMENTS

| | | | |
|---|---|---|---|
| 5,431,562 A | 7/1995 | Andreiko et al. | |
| D420,995 S | 2/2000 | Imamura | |
| D436,580 S | 1/2001 | Navano | |
| 6,315,553 B1 | 11/2001 | Sachdeva | |
| 6,540,512 B1 | 4/2003 | Sachdeva | |
| 6,696,073 B2 | 2/2004 | Boyce et al. | |
| 6,772,026 B2 | 8/2004 | Bradbury | |
| 6,932,842 B1 | 8/2005 | Litschko et al. | |
| 6,978,188 B1 | 12/2005 | Christensen | |
| 6,988,241 B1 | 1/2006 | Guttman | |
| 7,174,282 B2 | 2/2007 | Hollister et al. | |
| 7,187,790 B2 | 3/2007 | Sabol et al. | |
| D548,242 S | 8/2007 | Viegers | |
| D614,191 S | 4/2010 | Takano | |
| 7,747,305 B2 | 6/2010 | Dean et al. | |
| 7,756,314 B2 | 7/2010 | Karau et al. | |
| 7,799,077 B2 | 9/2010 | Lang | |
| D633,514 S | 3/2011 | Tokunaga | |
| D656,153 S | 3/2012 | Imamura | |
| 8,214,016 B2 * | 7/2012 | Lavallee | G06F 30/00 606/102 |
| 8,246,680 B2 | 8/2012 | Betz | |
| 8,265,949 B2 | 9/2012 | Haddad | |
| 8,275,594 B2 | 9/2012 | Lin | |
| 8,337,507 B2 | 12/2012 | Lang | |
| 8,394,142 B2 | 3/2013 | Bertagnoli | |
| 8,457,930 B2 | 6/2013 | Shroeder | |
| 8,532,806 B1 | 9/2013 | Masson | |
| 8,556,983 B2 | 10/2013 | Bojarski et al. | |
| 8,644,568 B1 | 2/2014 | Hoffman | |
| 8,735,773 B2 | 5/2014 | Lang | |
| 8,758,357 B2 | 6/2014 | Frey | |
| 8,775,133 B2 | 7/2014 | Schroeder | |
| 8,781,557 B2 | 7/2014 | Dean | |
| 8,843,229 B2 | 9/2014 | Vanasse | |
| 8,855,389 B1 | 10/2014 | Hoffman | |
| 8,870,889 B2 | 10/2014 | Frey | |
| 9,020,788 B2 | 4/2015 | Lang | |
| D735,231 S | 7/2015 | Omiya | |
| D737,309 S | 8/2015 | Kito | |
| 9,198,678 B2 | 12/2015 | Frey et al. | |
| 9,208,558 B2 | 12/2015 | Dean | |
| D757,025 S | 5/2016 | Kim | |
| D761,842 S | 7/2016 | Johnson | |
| 9,411,939 B2 | 8/2016 | Furrer | |
| 9,445,907 B2 | 9/2016 | Meridew | |
| 9,452,050 B2 | 9/2016 | Miles et al. | |
| D774,076 S | 12/2016 | Fuller | |
| 9,542,525 B2 | 1/2017 | Arisoy et al. | |
| 9,642,633 B2 | 5/2017 | Frey et al. | |
| 9,693,831 B2 | 7/2017 | Mosnier et al. | |
| 9,707,058 B2 | 7/2017 | Bassett | |
| 9,715,563 B1 | 7/2017 | Schroeder | |
| D797,760 S | 9/2017 | Tsujimura | |
| D797,766 S | 9/2017 | Ibsies | |
| D798,312 S | 9/2017 | Tsujimura | |
| 9,757,245 B2 | 9/2017 | O'Neil et al. | |
| D798,894 S | 10/2017 | Ibsies | |
| 9,775,680 B2 | 10/2017 | Bojarski et al. | |
| 9,782,228 B2 | 10/2017 | Mosnier et al. | |
| D812,628 S | 3/2018 | Okado | |
| 9,993,341 B2 | 6/2018 | Vanasse | |
| 10,034,676 B2 | 7/2018 | Donner | |
| D825,605 S | 8/2018 | Jann | |
| D826,977 S | 8/2018 | Nakajima | |
| 10,089,413 B2 | 10/2018 | Wirx-Speetjens et al. | |
| D841,675 S | 2/2019 | Hoffman | |
| 10,213,311 B2 | 2/2019 | Mafhouz | |
| D845,973 S | 4/2019 | Jaycobs | |
| D845,974 S | 4/2019 | Cooperman | |
| D847,165 S | 4/2019 | Kolbenheyer | |
| D848,468 S | 5/2019 | Ng | |
| D849,029 S | 5/2019 | Cooperman | |
| D849,773 S | 5/2019 | Jiang | |
| 10,292,770 B2 | 5/2019 | Ryan | |
| 10,299,863 B2 | 5/2019 | Grbic et al. | |
| D854,560 S | 7/2019 | Field | |
| D854,561 S | 7/2019 | Field | |
| 10,390,958 B2 | 8/2019 | Maclennan | |
| D860,237 S | 9/2019 | Li | |
| D860,238 S | 9/2019 | Bhardwaj | |
| D866,577 S | 11/2019 | Eisert | |
| D867,379 S | 11/2019 | Ang | |
| D867,389 S | 11/2019 | Jamison | |
| 10,463,433 B2 | 11/2019 | Turner et al. | |
| D870,762 S | 12/2019 | Mendoza | |
| 10,512,546 B2 | 12/2019 | Kamer et al. | |
| 10,517,681 B2 | 12/2019 | Roh et al. | |
| D872,117 S | 1/2020 | Kobayashi | |
| D872,756 S | 1/2020 | Howell | |
| D874,490 S | 2/2020 | Dodsworth | |
| D875,761 S | 2/2020 | Heffernan | |
| D876,454 S | 2/2020 | Knowles | |
| D876,462 S | 2/2020 | Li | |
| D877,167 S | 3/2020 | Knowles | |
| D879,112 S | 3/2020 | Hejazi | |
| 10,588,589 B2 | 3/2020 | Bregman-Amitai et al. | |
| 10,603,055 B2 | 3/2020 | Donner et al. | |

(56) References Cited

U.S. PATENT DOCUMENTS

| | | |
|---|---|---|
| D880,513 S | 4/2020 | Wang |
| D881,908 S | 4/2020 | Sunil |
| D881,910 S | 4/2020 | Lin |
| 10,621,289 B2 | 4/2020 | Schroeder |
| 10,631,988 B2 | 4/2020 | Arnold et al. |
| D884,008 S | 5/2020 | Thornberg |
| 10,646,236 B2 | 5/2020 | Donner et al. |
| 10,646,258 B2 | 5/2020 | Donner et al. |
| 10,736,698 B2 | 8/2020 | Bohl |
| 10,751,188 B2 | 8/2020 | Guo et al. |
| D896,825 S | 9/2020 | Abel |
| D896,828 S | 9/2020 | Linares |
| D898,054 S | 10/2020 | Everhart |
| D899,438 S | 10/2020 | Crafts |
| 10,806,597 B2 | 10/2020 | Sournac et al. |
| 10,902,944 B1 | 1/2021 | Casey et al. |
| D916,868 S | 4/2021 | Evangeliou |
| D916,879 S | 4/2021 | Mitsumori |
| D918,253 S | 5/2021 | Choe |
| 11,000,334 B1 | 5/2021 | Young |
| D921,675 S | 6/2021 | Kmak |
| D921,677 S | 6/2021 | Kmak |
| D921,687 S | 6/2021 | Kmak |
| D924,909 S | 7/2021 | Nasu |
| D925,567 S | 7/2021 | Hayamizu |
| D927,528 S | 8/2021 | Heisler |
| 11,083,586 B2 | 8/2021 | Cordonnier |
| 11,112,770 B2 | 9/2021 | Roh et al. |
| D933,692 S | 10/2021 | Smith |
| 11,166,764 B2 | 11/2021 | Roh et al. |
| D937,870 S | 12/2021 | Pinto |
| D937,876 S | 12/2021 | Harvey |
| D938,461 S | 12/2021 | Hoffman |
| D938,986 S | 12/2021 | Grossberg |
| D940,178 S | 1/2022 | Ang |
| D946,022 S | 3/2022 | Nuttbrown |
| D946,023 S | 3/2022 | Nuttbrown |
| D946,024 S | 3/2022 | Vogler-Ivashchanka |
| D946,616 S | 3/2022 | Tsai |
| D958,151 S | 7/2022 | Casey et al. |
| 11,376,076 B2 | 7/2022 | Casey et al. |
| 11,432,943 B2 | 9/2022 | Casey et al. |
| 11,439,514 B2 | 9/2022 | Casey et al. |
| 2004/0104512 A1 | 6/2004 | Eidenschink |
| 2005/0234555 A1 | 10/2005 | Sutton et al. |
| 2005/0273170 A1 | 12/2005 | Navarro et al. |
| 2005/0277934 A1* | 12/2005 | Vardiman .......... A61B 17/7083 606/915 |
| 2007/0272747 A1 | 11/2007 | Woods et al. |
| 2007/0276369 A1 | 11/2007 | Allard et al. |
| 2007/0276501 A1 | 11/2007 | Betz |
| 2008/0227047 A1 | 9/2008 | Lowe |
| 2009/0062739 A1 | 3/2009 | Anderson |
| 2010/0191088 A1 | 7/2010 | Anderson et al. |
| 2010/0217336 A1* | 8/2010 | Crawford .............. G16H 50/50 606/86 R |
| 2010/0324692 A1 | 12/2010 | Uthgenannt |
| 2011/0196451 A1 | 8/2011 | Hill |
| 2012/0150243 A9 | 6/2012 | Crawford et al. |
| 2012/0322018 A1 | 12/2012 | Lowe |
| 2013/0323669 A1 | 12/2013 | Lowe |
| 2014/0072608 A1 | 3/2014 | Karagkiozaki |
| 2014/0074438 A1 | 3/2014 | Furrer |
| 2014/0081659 A1 | 3/2014 | Nawana et al. |
| 2014/0086780 A1 | 3/2014 | Miller |
| 2014/0100886 A1 | 4/2014 | Woods |
| 2014/0135940 A1* | 5/2014 | Goldstein ............. A61B 17/15 623/22.21 |
| 2014/0164022 A1 | 6/2014 | Reed |
| 2014/0263674 A1 | 9/2014 | Cerveny |
| 2014/0277487 A1 | 9/2014 | Davenport et al. |
| 2014/0350614 A1 | 11/2014 | Frey |
| 2015/0079533 A1 | 3/2015 | Lowe |
| 2015/0089590 A1 | 3/2015 | Krishnan et al. |
| 2015/0105891 A1 | 4/2015 | Golway et al. |
| 2015/0199488 A1 | 7/2015 | Falchuk |
| 2015/0213225 A1 | 7/2015 | Amarasingham |
| 2015/0324490 A1 | 11/2015 | Page |
| 2015/0328004 A1 | 11/2015 | Mafhouz |
| 2015/0332018 A1 | 11/2015 | Rosen |
| 2016/0001039 A1 | 1/2016 | Armour et al. |
| 2016/0015465 A1 | 1/2016 | Steines et al. |
| 2016/0030067 A1 | 2/2016 | Frey et al. |
| 2016/0074048 A1 | 3/2016 | Pavlovskaia |
| 2016/0081810 A1 | 3/2016 | Reiley et al. |
| 2016/0117817 A1 | 4/2016 | Seel |
| 2016/0143744 A1 | 5/2016 | Bojarski et al. |
| 2016/0184054 A1 | 6/2016 | Lowe |
| 2016/0210374 A1 | 7/2016 | Mosnier et al. |
| 2016/0217268 A1 | 7/2016 | Otto |
| 2016/0242857 A1 | 8/2016 | Scholl |
| 2016/0300026 A1 | 10/2016 | Bogoni et al. |
| 2016/0354039 A1 | 12/2016 | Soto et al. |
| 2016/0354213 A1 | 12/2016 | Cowan |
| 2016/0378919 A1 | 12/2016 | McNutt et al. |
| 2017/0000566 A1 | 1/2017 | Gordon |
| 2017/0014169 A1 | 1/2017 | Dean |
| 2017/0020679 A1 | 1/2017 | Maclennan |
| 2017/0035514 A1 | 2/2017 | Fox et al. |
| 2017/0046486 A1* | 2/2017 | Cunningham ........ G06F 3/0482 |
| 2017/0061375 A1 | 3/2017 | Laster |
| 2017/0068792 A1 | 3/2017 | Reiner |
| 2017/0112548 A1 | 4/2017 | Alamin et al. |
| 2017/0135706 A1 | 5/2017 | Frey et al. |
| 2017/0143494 A1 | 5/2017 | Mahfouz |
| 2017/0143831 A1 | 5/2017 | Varanasi et al. |
| 2017/0196499 A1 | 7/2017 | Hunter |
| 2017/0216047 A1 | 8/2017 | Hawkes et al. |
| 2017/0220740 A1 | 8/2017 | D'Urso |
| 2017/0252107 A1 | 9/2017 | Turner et al. |
| 2017/0262595 A1 | 9/2017 | Vorhis |
| 2017/0340447 A1 | 11/2017 | Mahfouz |
| 2017/0354510 A1 | 12/2017 | O'Neil et al. |
| 2017/0367645 A1 | 12/2017 | Klinder |
| 2018/0008349 A1 | 1/2018 | Gillman |
| 2018/0113992 A1 | 4/2018 | Eltorai et al. |
| 2018/0116727 A1 | 5/2018 | Caldwell et al. |
| 2018/0168499 A1 | 6/2018 | Bergold |
| 2018/0168731 A1 | 6/2018 | Reid |
| 2018/0185075 A1 | 7/2018 | She |
| 2018/0233222 A1 | 8/2018 | Daley |
| 2018/0233225 A1 | 8/2018 | Experton |
| 2018/0250075 A1 | 9/2018 | Cho |
| 2018/0303552 A1 | 10/2018 | Ryan |
| 2018/0303616 A1 | 10/2018 | Bhattacharyya et al. |
| 2018/0308569 A1 | 10/2018 | Luellen |
| 2018/0338841 A1 | 11/2018 | Miller et al. |
| 2019/0065685 A1 | 2/2019 | Pickover |
| 2019/0069956 A1 | 3/2019 | Ryan et al. |
| 2019/0099221 A1 | 4/2019 | Schmidt et al. |
| 2019/0201106 A1 | 7/2019 | Siemionow |
| 2019/0262084 A1 | 8/2019 | Roh et al. |
| 2019/0266597 A1 | 8/2019 | Mohtar |
| 2019/0328929 A1 | 10/2019 | Kugler et al. |
| 2019/0333622 A1 | 10/2019 | Levin |
| 2019/0354693 A1 | 11/2019 | Yoon |
| 2019/0380792 A1 | 12/2019 | Poltaretskyi et al. |
| 2019/0388131 A1 | 12/2019 | Mehl et al. |
| 2020/0021570 A1 | 1/2020 | Lin |
| 2020/0078180 A1 | 3/2020 | Casey et al. |
| 2020/0085509 A1 | 3/2020 | Roh et al. |
| 2020/0170802 A1 | 6/2020 | Casey et al. |
| 2020/0258605 A1 | 8/2020 | Blechman |
| 2020/0261156 A1 | 8/2020 | Schmidt |
| 2020/0289288 A1 | 9/2020 | Müller et al. |
| 2020/0315708 A1 | 10/2020 | Mosnier et al. |
| 2021/0059822 A1 | 3/2021 | Casey et al. |
| 2021/0064605 A1 | 3/2021 | Balint |
| 2021/0145519 A1 | 5/2021 | Mosnier et al. |
| 2021/0169576 A1 | 6/2021 | Ryan et al. |
| 2021/0192759 A1 | 6/2021 | Lang |
| 2021/0210189 A1 | 7/2021 | Casey et al. |
| 2021/0287770 A1 | 9/2021 | Anderson |
| 2021/0382457 A1 | 12/2021 | Roh et al. |

(56) References Cited

U.S. PATENT DOCUMENTS

| | | | |
|---|---|---|---|
| 2022/0000625 A1 | 1/2022 | Cordonnier |
| 2022/0006642 A1 | 1/2022 | Maj et al. |
| 2022/0013211 A1 | 1/2022 | Steinberg et al. |
| 2022/0039965 A1 | 2/2022 | Casey et al. |
| 2022/0047402 A1 | 2/2022 | Casey et al. |
| 2022/0110686 A1 | 4/2022 | Roh et al. |
| 2022/0160405 A1 | 5/2022 | Casey et al. |
| 2022/0160518 A1 | 5/2022 | Casey et al. |
| 2023/0023440 A1 | 1/2023 | Casey et al. |

FOREIGN PATENT DOCUMENTS

| | | | | |
|---|---|---|---|---|
| CN | 204468348 U | 7/2015 | | |
| CN | 105796214 A | 7/2016 | | |
| CN | 106202861 | 12/2016 | | |
| CN | 107220933 | 9/2017 | | |
| CN | 108670506 A | 10/2018 | | |
| CN | 110575289 A | 12/2019 | | |
| CN | 111281613 A | 6/2020 | | |
| CN | 112155792 A | 1/2021 | | |
| CN | 113643790 | 11/2021 | | |
| EP | 3120796 A1 | 1/2017 | | |
| WO | 9507509 A1 | 3/1995 | | |
| WO | 2004110309 A2 | 12/2004 | | |
| WO | WO2008027549 | * | 3/2008 | ............ G06F 19/00 |
| WO | 2010151564 A1 | 12/2010 | | |
| WO | WO2011080260 | * | 7/2011 | ............ A61B 17/17 |
| WO | 2012154534 A1 | 11/2012 | | |
| WO | 2014180972 A2 | 11/2014 | | |
| WO | WO2016102025 | * | 6/2016 | ............ A61B 77/77 |
| WO | 2016172694 A1 | 10/2016 | | |
| WO | 2017116346 A1 | 7/2017 | | |
| WO | 2019112917 A1 | 6/2019 | | |
| WO | 2019148154 A1 | 8/2019 | | |
| WO | 2019165152 A1 | 8/2019 | | |
| WO | 2019241167 A1 | 12/2019 | | |
| WO | 2020055874 A1 | 3/2020 | | |
| WO | 2022045956 A1 | 3/2022 | | |

OTHER PUBLICATIONS

Harrysson, O. et al., "Custom-designed orthopedic implants evaluated using finite element analysis of patient-specific computed tomography data: femoral-component case study." BMC Musculoskeletal Disorders. Dec. 2007, 8:91, 10 pages.
International Search Report and Written Opinion for International Application No. PCT/US22/32624, dated Oct. 28, 2022, 16 pages.
International Search Report and Written Opinion for International Application No. PCT/US22/35232, dated Nov. 16, 2022, 24 pages.
International Search Report and Written Opinion for International Application No. PCT/US22/36007, dated Oct. 11, 2022, 14 pages.
International Search Report and Written Opinion for International Application No. PCT/US22/37500, dated Dec. 28, 2022, 19 pages.
International Search Report and Written Opinion for International Application No. PCT/US22/37640, dated Nov. 15, 2022, 13 pages.
International Search Report and Written Opinion for International Application No. PCT/US22/42188, dated Dec. 29, 2022, 19 pages.
Office Action for Japanese Application No. 2020-550591, dated Dec. 26, 2022, 4 pages, English Translation.
U.S. Appl. No. 18/071,555 for Casey et al., filed Nov. 29, 2022.
U.S. Appl. No. 18/071,566 for Casey et al., filed Nov. 29, 2022.
Endo, Kenji et al. "Measurement of whole spine sagittal alignment using the SLOT radiography of the SONIALVISION safire series clinical application." Medical Now, No. 78; Aug. 2015, 4 pages.
Eshkalak, S.K. et al., "The role of three-dimensional printing in healthcare and medicine." Materials and Design 194, Jul. 10, 20202, 15 pages.
Extended European Search Report for European Application No. 18885367.5, dated Aug. 16, 2021, 8 pages.
Extended European Search Report for European Application No. 19859930.0, dated Jun. 22, 2022, 7 pages.
International Search Report and Written Opinion for International Application No. PCT/US19/50885, dated Jan. 28, 2020, 21 pages.
International Search Report and Written Opinion for International Application No. PCT/US19/63855, dated Feb. 14, 2020, 15 pages.
International Search Report and Written Opinion for International Application No. PCT/US21/44878, dated Nov. 16, 2021, 18 pages.
International Search Report and Written Opinion for International Application No. PCT/US21/45503, dated Jan. 11, 2022, 19 pages.
International Search Report and Written Opinion for International Patent Application No. PCT/US21/60074, dated Mar. 17, 2022, 21 pages.
International Search Report and Written Opinion for International Patent Application No. PCT/US2018/063530, dated Feb. 12, 2019, 16 pages.
International Search Report and Written Opinion for International Patent Application No. PCT/US21/12065, dated Apr. 29, 2021, 19 pages.
International Search Report and Written Opinion for International Patent Application No. PCT/US21/59837, dated Feb. 7, 2022, 19 pages.
Majdouline et al., "Preoperative assessment and evaluation of instrumentation strategies for the treatment of adolescent idiopathic scoliosis: computer simulation and optimization." Scoliosis 7, 21 (2012), pp. 1-8.
Materialise Mimics, "Efficiently turn scans into accurate virtual 3D models," Retrieved on Nov. 1, 2019 at www. materialize.com/en/medical/software/mimics, 1 page.
Pimenta, Dr. Luiz, "Current Surgical Strategies to Restore Proper Sagittal Alignment," Journal of Spine 2015, vol. 4, Issue 4, 2 pages.
Pruthi, G. et al., "Comprehensive review of guidelines to practice prosthodontic and implant procedures during COVID-19 pandemic." Journal of Oral Biology and Craniofacial Research 10, Oct. 17, 2020, 8 pages.
U.S. Appl. No. 15/958,409 for Ryan filed Apr. 21, 2017.
U.S. Appl. No. 17/463,054 for Casey et al., filed Aug. 31, 2021.
U.S. Appl. No. 17/518,524 for Cordonnier, filed Nov. 3, 2021.
U.S. Appl. No. 17/678,874 for Cordonnier, filed Feb. 23, 2022.
U.S. Appl. No. 17/702,591 for Roh et al., filed Mar. 23, 2022.
U.S. Appl. No. 17/835,777 for Cordonnier, filed Jun. 8, 2022.
U.S. Appl. No. 17/838,727 for Casey et al., filed Jun. 13, 2022.
U.S. Appl. No. 17/842,242 for Cordonnier, filed Jun. 16, 2022.
U.S. Appl. No. 17/851,487 for Cordonnier, filed, Jun. 28, 2022.
U.S. Appl. No. 17/856,625 for Cordonnier, filed, Jul. 1, 2022.
U.S. Appl. No. 17/867,621 for Cordonnier, filed, Jul. 18, 2022.
U.S. Appl. No. 17/875,699 for Casey et al., filed Jul. 28, 2022.
U.S. Appl. No. 17/878,633 for Cordonnier, filed, Aug. 1, 2022.
U.S. Appl. No. 17/880,277 for Casey et al., filed, Aug. 3, 2022.

* cited by examiner

| Screw Type and Size | Thread Diameter, $d_1$ | Core Diameter, $d_s$ | Crest Width, e | Thread Pitch, P | Leading Edge Radius, $r_4$ | Trailing Edge Radius, $r_5$ | Leading Edge Angle, $\alpha$ | Trailing Edge Angle, $\beta$ |
|---|---|---|---|---|---|---|---|---|
| HA 1.5 | 1.50 +0.00/−0.15 | 1.10 +0.00/−0.10 | 0.1 | 0.5 | 0.3 | 0.1 | 35 | 3 |
| HA 2.0 | 2.00 +0.00/−0.15 | 1.30 +0.00/−0.10 | 0.1 | 0.6 | 0.4 | 0.1 | 35 | 3 |
| HA 2.7 | 2.70 +0.00/−0.15 | 1.90 +0.00/−0.10 | 0.1 | 1.0 | 0.6 | 0.2 | 35 | 3 |
| HA 3.5 | 3.50 +0.00/−0.15 | 2.40 +0.00/−0.15 | 0.1 | 1.25 | 0.8 | 0.2 | 35 | 3 |
| HA 4.0 | 4.00 +0.00/−0.15 | 2.90 +0.00/−0.15 | 0.1 | 1.5 | 0.8 | 0.2 | 35 | 3 |
| HA 4.5 | 4.50 +0.00/−0.15 | 3.00 +0.00/−0.15 | 0.1 | 1.75 | 1.0 | 0.3 | 35 | 3 |
| HA 5.0 | 5.00 +0.00/−0.15 | 3.50 +0.00/−0.15 | 0.1 | 1.75 | 1.0 | 0.3 | 35 | 3 |

SYSTEMS AND METHODS FOR PHYSICIAN DESIGNED SURGICAL PROCEDURES

CROSS-REFERENCE TO RELATED APPLICATIONS

This application is a continuation of U.S. patent application Ser. No. 17/702,591, filed on Mar. 23, 2022, titled "SYSTEMS AND METHODS FOR PHYSICIAN DESIGNED SURGICAL PROCEDURES," which is a continuation of U.S. patent application Ser. No. 17/497,546, filed on Oct. 8, 2021, titled "SYSTEMS AND METHODS FOR ASSISTING AND AUGMENTING SURGICAL PROCEDURES," which is a continuation of U.S. patent application Ser. No. 16/048,167, filed on Jul. 27, 2018 (now U.S. Pat. No. 11,166,764), titled "SYSTEMS AND METHODS FOR ASSISTING AND AUGMENTING SURGICAL PROCEDURES," which claims priority to U.S. Provisional Patent Application No. 62/537,869, filed on Jul. 27, 2017, titled "SYSTEMS AND METHODS OF PROVIDING ASSISTANCE DURING A SPINAL SURGERY," which are herein incorporated by reference in their entireties. All of these applications and patent are incorporated by reference in their entireties.

TECHNICAL FIELD

The present disclosure is generally related to providing surgical assistance to a surgeon, and more particularly for providing surgical assistance for a surgical procedure.

BACKGROUND

Assessing spinal deformity is of tremendous importance for a number of disorders affecting human spine. A pedicle is a dense stem-like structure that projects from the posterior of a vertebra. There are two pedicles per vertebra that connect to structures like a lamina and a vertebral arch. Conventionally available screws, used in spinal surgeries, are poly-axial pedicle screws made of titanium. Titanium is chosen as it is highly resistant to corrosion and fatigue, and is easily visible in MRI images.

The pedicle screws were originally placed via a free-hand technique. Surgeons performing spinal surgeries merely rely on their experience and knowledge of known specific paths for performing the spinal surgeries. The free-hand techniques used by spinal surgeons rely on spinal anatomy of a patient. The spinal surgeon relies on pre-operative imaging and intra-operative anatomical landmarks for performing the spinal surgery. Assistive fluoroscopy and navigation are helpful in that they guide pedicle screw placement more or less in a real-time, but are limited by time and costs involved in fluoroscopy, and significant radiation exposure during fluoroscopy.

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also correspond to implementations of the claimed technology.

BRIEF DESCRIPTION OF THE DRAWINGS

The accompanying drawings illustrate various embodiments of systems, methods, and embodiments of various other aspects of the disclosure. Any person with ordinary skills in the art will appreciate that the illustrated element boundaries (e.g. boxes, groups of boxes, or other shapes) in the figures represent one example of the boundaries. It may be that in some examples one element may be designed as multiple elements or that multiple elements may be designed as one element. In some examples, an element shown as an internal component of one element may be implemented as an external component in another, and vice versa. Furthermore, elements may not be drawn to scale. Non-limiting and non-exhaustive descriptions are described with reference to the following drawings. The components in the figures are not necessarily to scale, emphasis instead being placed upon illustrating principles.

DETAILED DESCRIPTION

Embodiments of the present disclosure will be described more fully hereinafter with reference to the accompanying drawings in which like numerals represent like elements throughout the several figures, and in which example embodiments are shown. Embodiments of the claims may, however, be embodied in many different forms and should not be construed as limited to the embodiments set forth herein. The examples set forth herein are non-limiting examples and are merely examples among other possible examples.

The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items.

It must also be noted that as used herein and in the appended claims, the singular forms "a," "an," and "the" include plural references unless the context clearly dictates otherwise. Although any systems and methods similar or equivalent to those described herein can be used in the practice or testing of embodiments of the present disclosure, the preferred, systems and methods are now described.

Figure 1A:
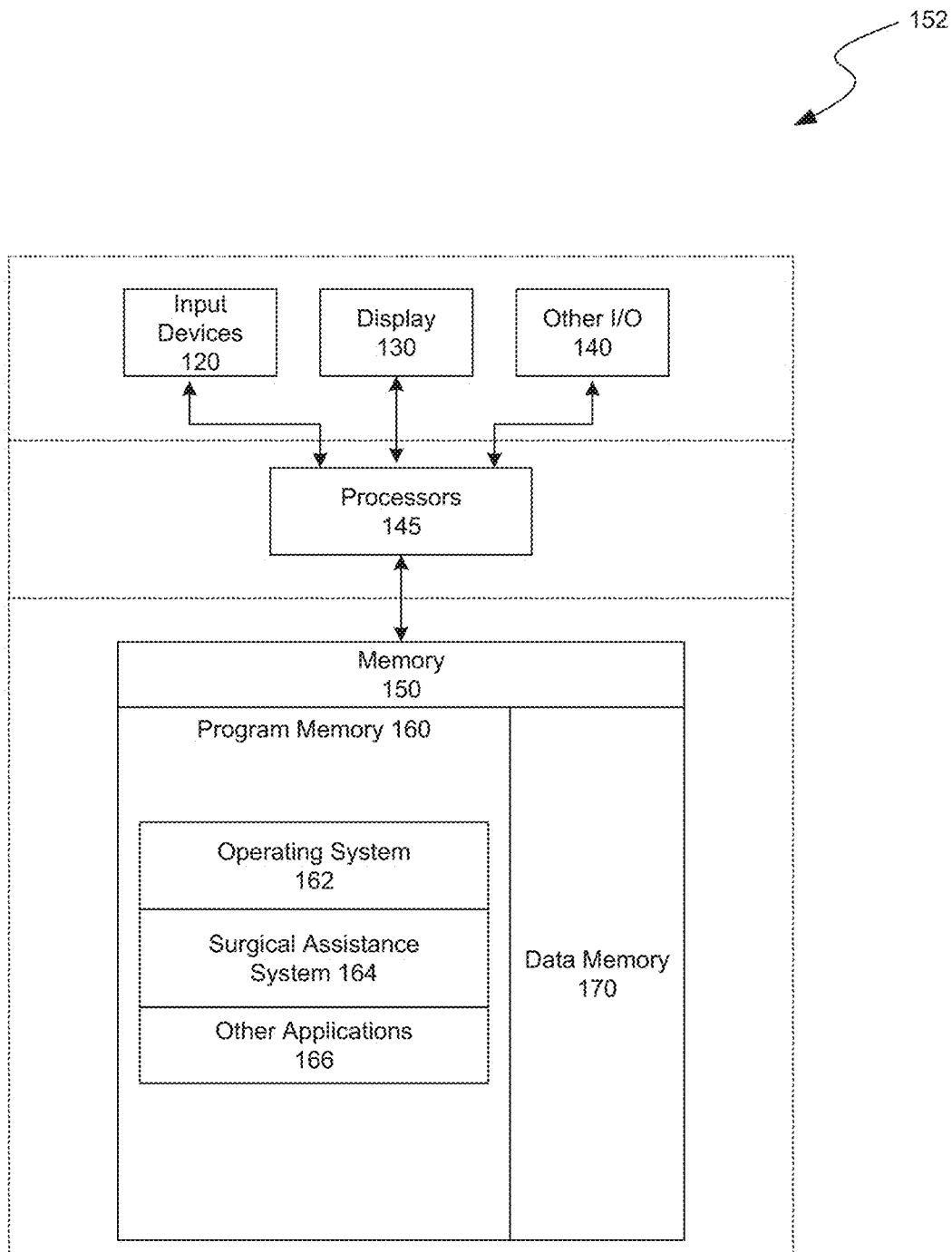
FIG. 1A illustrates a system for providing assistance prior to or during an implant surgery, according to an embodiment.

FIG. 1A illustrates a system 152 for providing assistance prior to or during an implant surgery, according to an embodiment. The system 152 can improve surgeries that involve implants by guiding selection and application of implants, delivery instruments, navigation tools, or the like. The system 152 can comprise hardware components that improve surgeries using, for example, a surgical assistance system 164. In various implementations, the surgical assistance system 164 can obtain implant surgery information, converting the implant surgery information into a form compatible with an analysis procedure, applying the analysis procedure to obtain results, and using the results to provide a configuration for the implant surgery.

An implant configuration can include characteristics of an implant such as various dimensions, angles, materials, application features (e.g., implant sizes, implant functionality, anchoring features, suture type, etc.), and/or aspects of applying the implant such as insertion point, delivery path, implant position/angle, rotation, amounts of force to apply (e.g., torque applied to a screw, rotational speed of a screw, rate of expansion of expandable implants, and so forth), etc. In some implementations, the implant surgery information can include images of a target area, such as MRI scans of a spine, patient information such as sex, weight, etc., or a surgeon's pre-operative plan. The surgical assistance system 164 can convert the implant surgery information, for example, by converting images into arrays of integers or histograms, entering patient information into feature vectors, or extracting values from the pre-operative plan.

In some implementations, surgical assistance system 164 can analyze one or more images of a patient to identify one or more features of interest. The features of interest can include, without limitation, implantation sites, targeted features, non-targeted features, access paths, anatomical structures, or combinations thereof. The implantation sites can be determined based upon one or more of risk factors, patient information, surgical information, or combinations thereof. The risk factors can be determined by the surgical assistant system based upon the patient's medical history. For example, if the patient is susceptible to infections, the surgical assistant system 164 can recommend a minimally invasive procedure whereas the surgical assistant system may recommend open procedure access paths for patients less susceptible to infection. In some implementations, the physician can provide the risk factors before or during the procedure. Patient information can include, without limitation, patient sex, age, health rating, or the like. The surgical information can include available navigation systems, robotic surgery platforms, access tools, surgery kits, or the like.

In some implementations, surgical assistance system 164 can apply analysis procedures by supplying the converted implant surgery information to a machine learning model trained to select implant configurations. For example, a neural network model can be trained to select pedicle screw configurations for a spinal surgery. The neural network can be trained with training items each comprising a set of images scans (e.g. camera, MRI, CT, x-ray, etc.) and patient information, an implant configuration used in the surgery, and/or a scored surgery outcome resulting from one or more of: surgeon feedback, patient recovery level, recovery time, results after a set number of years, etc. This neural network can receive the converted surgery information and provide output indicating the pedicle screw configuration.

In other implementations, surgical assistance system 164 can apply the analysis procedure by A) localizing and classifying a surgery target, B) segmenting the target to determine boundaries, C) localizing optimal implant insertion points, D) identifying target structures (e.g. pedicles and isthmus), and/or computing implant configurations based on results of A-D.

In yet further implementations, surgical assistance system 164 can apply the analysis procedure by building a virtual model of a surgery target area, localizing and classifying areas of interest within the virtual model, segmenting areas of interest, localizing insertion points, and computing implant configurations by simulating implant insertions in the virtual model. Each of the individual steps of these implementations can be accomplished using a machine learning model trained (as discussed below) to identify appropriate results for that step or by applying a corresponding algorithm. For example, an algorithm can measure an isthmus by determining an isthmus width in various images and tracking the minimal value across the images in different planes.

In another example, surgical assistance system 164 can apply the analysis procedure by performing a finite element analysis on a generated three-dimensional model (e.g., a model of the patient's anatomy) to assess stresses, strains, deformation characteristics (e.g., load deformation characteristics), fracture characteristics (e.g., fracture toughness), fatigue life, etc. A virtual representation of the implant or other devices could be generated. The surgical assistance system 164 can generate a three-dimensional mesh to analyze the model. Machine learning techniques to create an optimized mesh based on a dataset of vertebrae or other bones and implants or other devices. After performing the analysis, the results could be used to refine the selection of screws or other implant components.

The surgical assistance system 164 can incorporate results from the analysis procedure in suggestions for the implant surgery. For example, the results can be used to indicate suggested implants for a procedure, to annotate an image with suggested insertions points and angles, to generate a virtual reality or augmented reality representation including the suggested implant configurations, to provide warnings or other feedback to surgeons during a procedure, to automatically order the necessary implants, to generate surgical technique information (e.g., insertion forces/torques, imaging techniques, delivery instrument information, or the like), etc.

The surgical assistance system 164 can improve the efficiency, precision, and/or efficacy of implant surgeries by providing more optimal implant configuration guidance. This can reduce operational risks and costs produced by surgical complications, reduce the resources required for preoperative planning efforts, and reduce the need for extensive implant variety to be prepared prior to an implant surgery. The surgical assistance system 164 provides increased precision and efficiency for patients and surgeons.

In orthopedic surgeries, the surgical assistance system 164 can select or recommend implants (e.g., permanent implants, removable implants, etc.), surgical techniques, patient treatment plans, or the like. For example, the implants can be joint replacements, hip implants, removable bone screws, or the like. The surgical techniques can include access instruments selected based on one or more criteria, such as risk of adverse events, optical implant position, protected zones (e.g., zones with nerve tissue), or the like. In spinal surgeries, the surgical assistance system 164 can reduce incorrect selection of pedicle screw types, dimensions, and trajectories while making surgeons more efficient and precise, as compared to existing surgical procedures.

The surgical assistance system 164 can also improve surgical robotics/navigation systems, providing improved intelligence for selecting implant application parameters. For example, the surgical assistance system 164 empowers surgical robots and navigation systems for spinal surgeries to increase procedure efficiency and reduce surgery duration by providing information on types and sizes, along with expected insertion angles. In addition, hospitals benefit from reduced surgery durations and reduced costs of purchasing, shipping, and storing alternative implant options. Medical imaging and viewing technologies can integrate with the surgical assistance system 164, to provide more intelligent and intuitive results.

The surgical assistance system 164 can be incorporated in system 152, which can include one or more input devices 120 that provide input to the processor(s) 145 (e.g. CPU(s), GPU(s), HPU(s), etc.), notifying it of actions. The actions can be mediated by a hardware controller that interprets the signals received from the input device and communicates the information to the processors 145 using a communication protocol. Input devices 120 include, for example, a mouse, a keyboard, a touchscreen, an infrared sensor, a touchpad, a wearable input device, a camera- or image-based input device, a microphone, or other user input devices.

Processors 145 can be a single processing unit or multiple processing units in a device or distributed across multiple devices. Processors 145 can be coupled to other hardware devices, for example, with the use of a bus, such as a PCI bus or SCSI bus. The processors 145 can communicate with a hardware controller for devices, such as for a display 130. Display 130 can be used to display text and graphics. In some implementations, display 130 provides graphical and textual visual feedback to a user. In some implementations, display 130 includes the input device as part of the display, such as when the input device is a touchscreen or is equipped with an eye direction monitoring system. In some implementations, the display is separate from the input device. Examples of display devices are: an LCD display screen, an LED display screen, a projected, holographic, or augmented reality display (such as a heads-up display device or a head-mounted device), and so on. Other I/O devices 140 can also be coupled to the processor, such as a network card, video card, audio card, USB, firewire or other external device, camera, printer, speakers, CD-ROM drive, DVD drive, disk drive, or Blu-Ray device. Other I/O 140 can also include input ports for information from directly connected medical equipment such as MRI machines, X-Ray machines, etc. Other I/O 140 can further include input ports for receiving data from these types of machine from other sources, such as across a network or from previously captured data, e.g. stored in a database.

In some implementations, the system 152 also includes a communication device capable of communicating wirelessly or wire-based with a network node. The communication device can communicate with another device or a server through a network using, for example, TCP/IP protocols. System 152 can utilize the communication device to distribute operations across multiple network devices.

The processors 145 can have access to a memory 150 in a device or distributed across multiple devices. A memory includes one or more of various hardware devices for volatile and non-volatile storage, and can include both read-only and writable memory. For example, a memory can comprise random access memory (RAM), various caches, CPU registers, read-only memory (ROM), and writable non-volatile memory, such as flash memory, hard drives, floppy disks, CDs, DVDs, magnetic storage devices, tape drives, device buffers, and so forth. A memory is not a propagating signal divorced from underlying hardware; a memory is thus non-transitory. Memory 150 can include program memory 160 that stores programs and software, such as an operating system 162, surgical assistance system 164, and other application programs 166. Memory 150 can also include data memory 170 that can include, e.g. implant surgery information, configuration data, settings, user options or preferences, etc., which can be provided to the program memory 160 or any element of the system 152.

Some implementations can be operational with numerous other computing system environments or configurations. Examples of computing systems, environments, and/or configurations that may be suitable for use with the technology include, but are not limited to, personal computers, server computers, handheld or laptop devices, cellular telephones, wearable electronics, tablet devices, multiprocessor systems, microprocessor-based systems, programmable consumer electronics, network PCs, minicomputers, mainframe computers, distributed computing environments that include any of the above systems or devices, or the like.

Figure 1B:
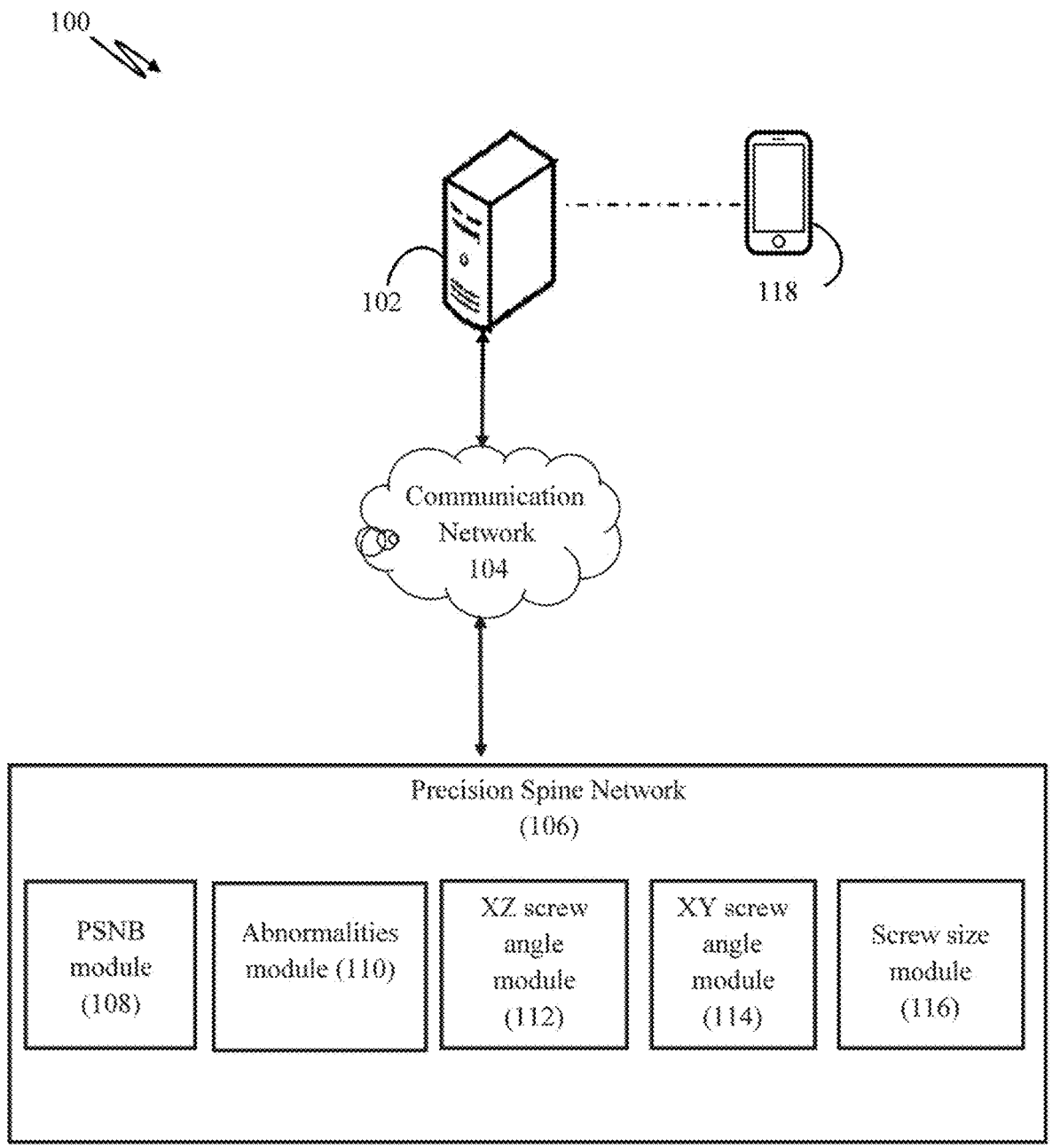
FIG. 1B illustrates a network connection diagram 100 of an implant surgery assistance system for providing assistance prior to or during an implant surgery, according to an embodiment.

FIG. 1B illustrates a network connection diagram 100 of a system 102 for providing assistance to a surgeon during a spinal surgery, according to an embodiment. The system 102 may be connected to a communication network 104. The communication network 104 may further be connected with a network in the form of a precision spine network 106 for allowing data transfer between the system 102 and the precision spine network 106.

The communication network 104 may be a wired and/or a wireless network. The communication network 104, if wireless, may be implemented using communication techniques such as Visible Light Communication (VLC), Worldwide Interoperability for Microwave Access (WiMAX), Long term evolution (LTE), Wireless local area network (WLAN), Infrared (IR) communication, Public Switched Telephone Network (PSTN), Radio waves, and other communication techniques known in the art.

In one embodiment, the precision spine network 106 may be implemented as a facility over "the cloud" and may include a group of modules. The group of modules may include a Precision Spine Network Base (PSNB) module 108, an abnormalities module 110, an XZ screw angle module 112, an XY screw module 114, and a screw size module 116.

The PSNB module 108 may be configured to store images of patients and types of spinal screws, required in spinal surgeries. In some implementations, a similar module can be used for other types of surgeries. While the PSNB is referred to below, in each instance other similar modules can be used for other types of surgeries. For example, a Precision Knee Network Based can be used to assist in anterior cruciate ligament (ACL) replacement surgeries. The images may be any of camera images, Magnetic Resonance Imaging (MRI) images, ultrasound images, Computerized Aided Tomography (CAT) scan images, Positron Emission Tomography (PET) images, and X-Ray images. In one case, the images may be analyzed to identify abnormalities and salient features in the images, for performing spinal surgeries on the patients. In some implementations, the PSNB module 108 can store additional implant surgery information, such as patient information, (e.g. sex, age, height, weight, type of pathology, occupation, activity level, tissue information, health rating, etc.), specifics of implant systems (e.g. types and dimensions), availability of available implants, aspects of a surgeon's preoperative plan (e.g. surgeon's initial implant configuration, detection and measurement of the patient's anatomy on images, etc.), etc. In some implementations, the PSNB module 108 can convert the implant surgery information into formats useable for implant suggestion models and algorithms. For example, the implant surgery information can be tagged with particular identifiers for formulas or can be converted into numerical representations suitable for supplying to a machine learning model.

The abnormalities module 110 may measure distances between a number of salient features of one vertebra with salient features of another vertebra, for identifying disk pinches or bulges. Based on the identified disk pinches or bulges, herniated disks may be identified in the patients. It should be obvious to those skilled in the art, that given a wide variety of salient features and geometric rules, many spinal abnormalities could be identified. If the spinal abnormalities are identified, the PSNB module 108 may graphically identify areas having the spinal abnormalities and may send such information to a user device 118.

In one embodiment, information related to spinal surgeries may be displayed through a Graphical User Interface (GUI) of the user device 118, as illustrated using FIG. 1B. A smart phone is shown as the user device 118 in FIG. 1B, as an example. Further, the user device 118 may be any other device including a GUI, for example, a laptop, desktop, tablet, phablet, or other such devices known in the art.

The XZ screw angle module 112 may determine an XZ angle of a spinal screw or other implant to be used during the surgery. Further, the XY screw angle module 114 may determine an XY angle of the implant. The XZ screw angle module 112 and the XY screw angle module 114 may determine a position entry point for at least one spinal screw. The XZ screw angle module 112 and the XY screw angle module 114 may graphically represent the identified data and may send such information to the user device 118.

The screw size module 116 may be used to determine a screw diameter (e.g., a maximum screw diameter) and a length of the screw based on the salient features identified from the images of the patients.

In some implementations, the XZ screw angle module 112, the XY screw angle module 114, and the screw size module 116 can identify implant configurations for other types of implants in addition to, or other than screws (e.g., pedicle screws, facet screws, etc.) such as cages, plates, rods, disks, fusions devices, spacers, rods, expandable devices, etc. In addition, these modules may suggest implant configurations in relation to references other than an X, Y, Z, coordinate system. For example, in a spinal surgery, the suggestions can be in reference to the sagittal plane, mid-sagittal plane, coronal plane, frontal plane, or transverse plane. As another example, in an ACL replacement surgery, the suggestions can be an angle for a tibial tunnel in reference to the frontal plane of the femur. In various implementations, the XZ screw angle module 112, the XY screw angle module 114, or screw size module 116 can identify implant configurations using machine learning modules, algorithms, or combinations thereof, as described below in relation to FIGS. 6-9.

Figure 2:
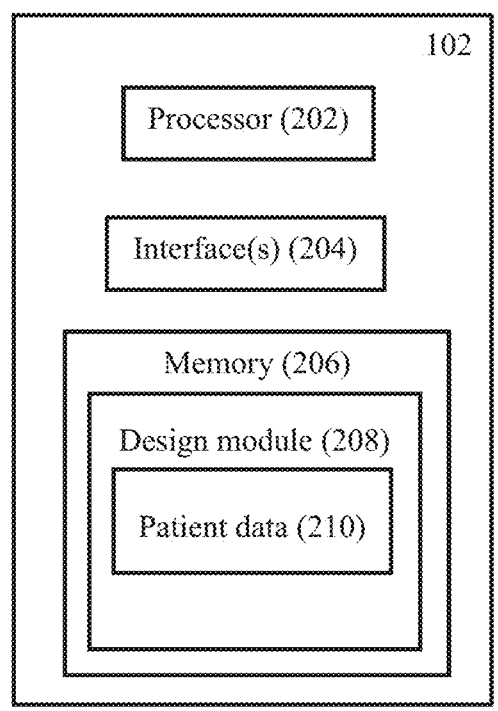
FIG. 2 illustrates a block diagram showing components of an implant surgery assistance system, according to an embodiment.

In one embodiment, referring to FIG. 2, a block diagram showing different components of the system 102 is explained. The system 102 includes a processor 202, interface(s) 204, and a memory 206. The processor 202 may execute an algorithm stored in the memory 206 for augmenting an implant surgery, e.g. by providing assistance to a surgeon during a spinal or other implant surgery, by providing controls to a robotic apparatus (e.g., robotic surgery systems, navigation system, etc.) for an implant surgery or by generating suggestions for implant configurations to be used in an implant surgery. The processor 202 may also be configured to decode and execute any instructions received from one or more other electronic devices or server(s). The processor 202 may include one or more general purpose processors (e.g., INTEL® or Advanced Micro Devices® (AMD) microprocessors) and/or one or more special purpose processors (e.g., digital signal processors or Xilinx® System On Chip (SOC) Field Programmable Gate Array (FPGA) processor). The processor 202 may be configured to execute one or more computer-readable program instructions, such as program instructions to carry out any of the functions described in this description.

The interface(s) 204 may help a user to interact with the system 102. The user may be any of an operator, a technician, a doctor, a doctor's assistant, or another automated system controlled by the system 102. The interface(s) 204 of the system 102 may either accept an input from the user or provide an output to the user, or may perform both the actions. The interface(s) 204 may either be a Command Line Interface (CLI), Graphical User Interface (GUI), or a voice interface.

The memory 206 may include, but is not limited to, fixed (hard) drives, magnetic tape, floppy diskettes, optical disks, Compact Disc Read-Only Memories (CD-ROMs), and magneto-optical disks, semiconductor memories, such as ROMs, Random Access Memories (RAMs), Programmable Read-Only Memories (PROMs), Erasable PROMs (EPROMs), Electrically Erasable PROMs (EEPROMs), flash memory, magnetic or optical cards, or other type of media/machine-readable medium suitable for storing electronic instructions.

The memory 206 may include modules, implemented as programmed instructions executed by the processor 202. In one case, the memory 206 may include a design module 208 for receiving information from the abnormalities module 110. The design module 208 may poll the surgeon for an information request. The design module 208 may allow the surgeon to design the spinal screw and change the generated implant configurations, such as the entry point (e.g., entry point into the patient, entry points into a vertebra, entry points to the implantation site, etc.), and screw or other implant angles in any of various planes. If the surgeon changes the entry point or angles, the system can automatically update other features of the implant configuration to account for the changes, such as the implant dimensions (e.g. screw diameter, thread pitch, or length). The design module 208 may include patient data 210. The patient data 210 may include images of patients and may allow the surgeon to identify the patients. A patient may refer to a person on whom and operations is to be performed. The patient data 210 may include images of patients, received from the user device 118.

In one embodiment, areas of interest may be defined in diagnostic data of a patient. In one case, the system 102 may determine the areas of interest based on pre-defined rules or using machine learning models, as described below in relation to FIGS. 6-9. In another case, the areas of interest may be defined based on a surgeon's input. In one case, the diagnostic data may include images of the patient. The images may be any of camera images, Magnetic Resonance Imaging (MRI) images, ultrasound images, Computerized Aided Tomography (CAT) scan images, Positron Emission Tomography (PET) images, and X-Ray images. In one case, the images of the patients may be stored in the patient surgeon database 210.

Figure 3A:
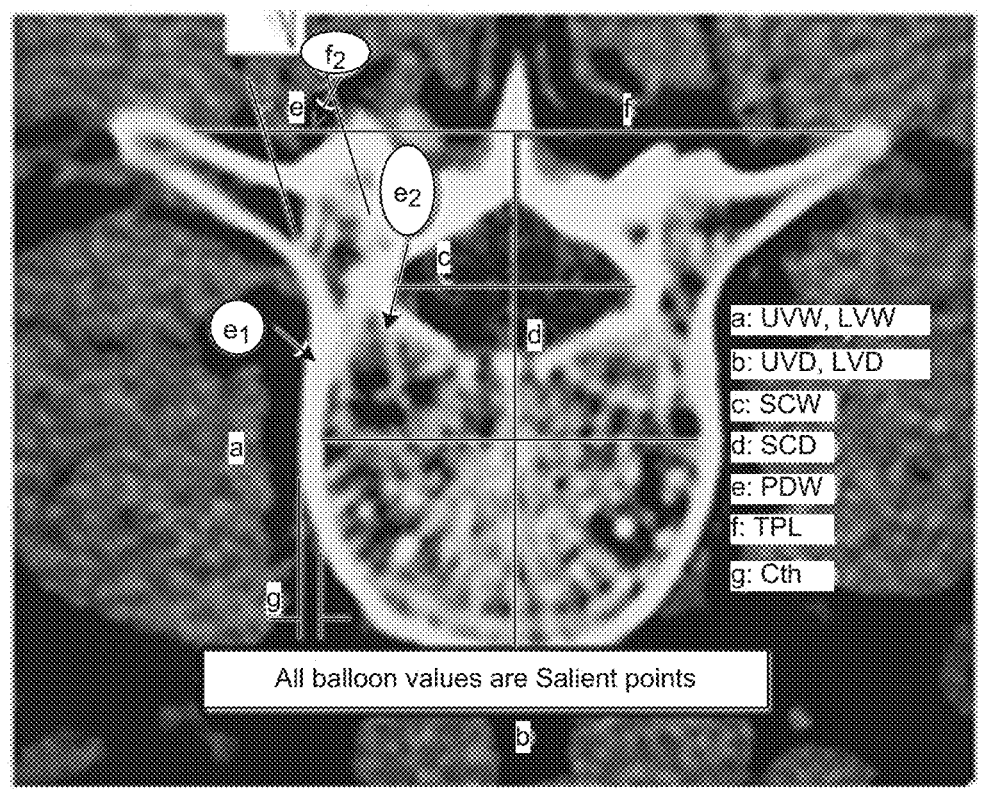
FIG. 3A shows salient points presented in a top view of a vertebra of the patient, according to an embodiment.
Figure 3B:
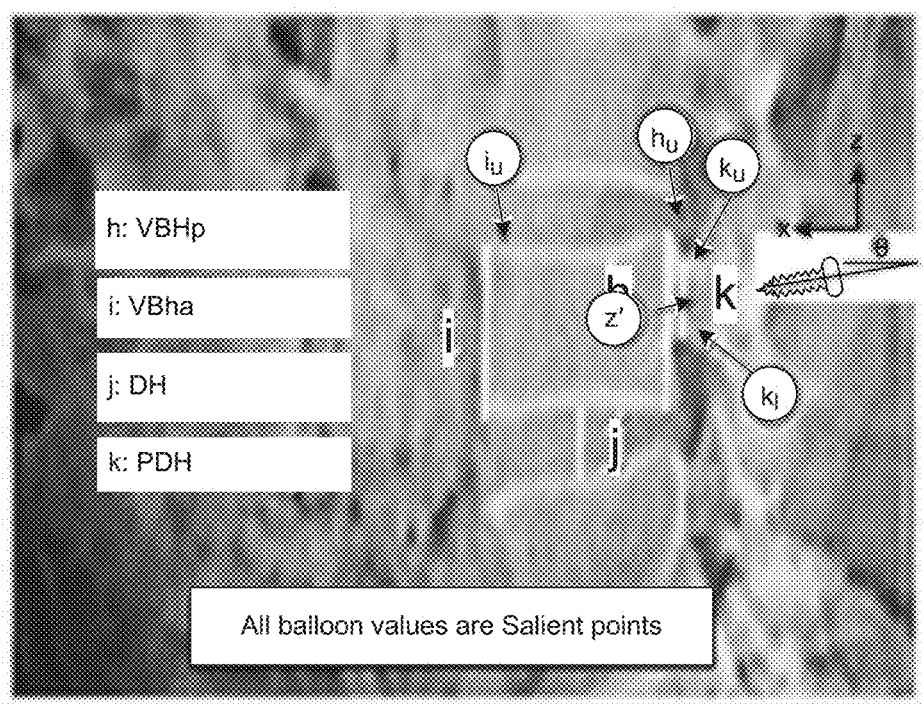
FIG. 3B shows salient points present in a side view of the vertebra of the patient, according to an embodiment.

Post defining the areas of interest, a screw bone type may be defined based on various models and/or the surgeon's input. Successively, salient features of the areas of interest may be identified in the images of the patients, e.g. by applying the procedures described below. FIG. 3A shows salient points present in a top view of a vertebra of the patient, according to an embodiment. The salient points are shown as bubbles i.e. '$e_1$,' '$e_2$,' and '$f_2$.' Further, FIG. 3B shows salient points present in a side view of the vertebra of the patient, according to an embodiment. The salient points are shown as bubbles i.e. '$k_l$,' '$k_u$,' '$h_u$,' '$i_m$,' and '$z$.'

Figure 4A:
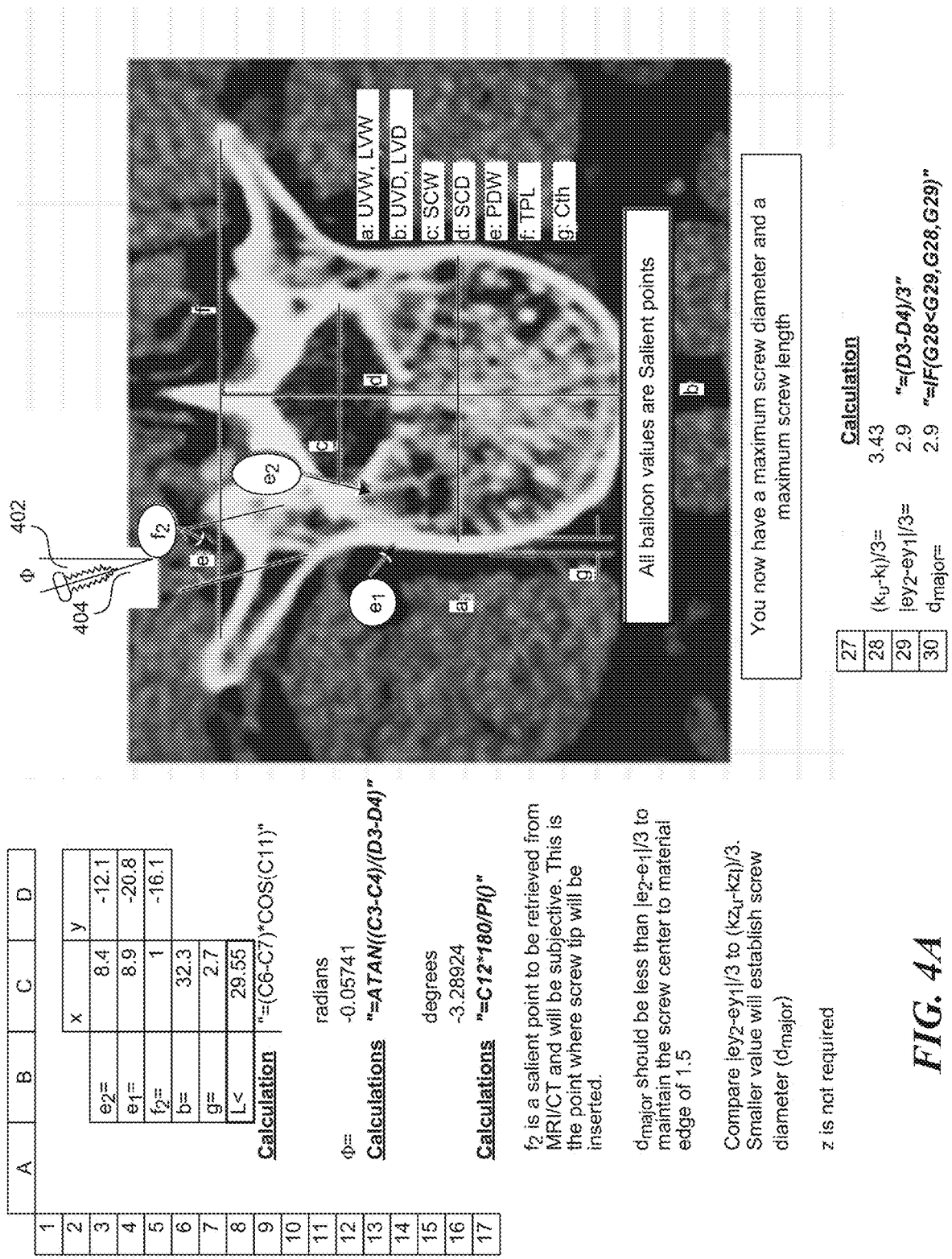
FIG. 4A illustrates computations for determining an XZ angle for a spinal screw, according to an embodiment.

Successively, based on the salient points of the areas of interest, the system 102 may determine implant configurations (e.g. angles and entry point, implant orientation, implant movement, etc.) using the analysis procedures. FIG. 4A illustrates computations for determining the XZ angle ($\phi$) 402 using the salient points, according to an embodiment. It should be noted that positions of X and Y co-ordinates of the regions of interest may be determined based on a location of at least one salient feature present in the image.

Figure 4B:
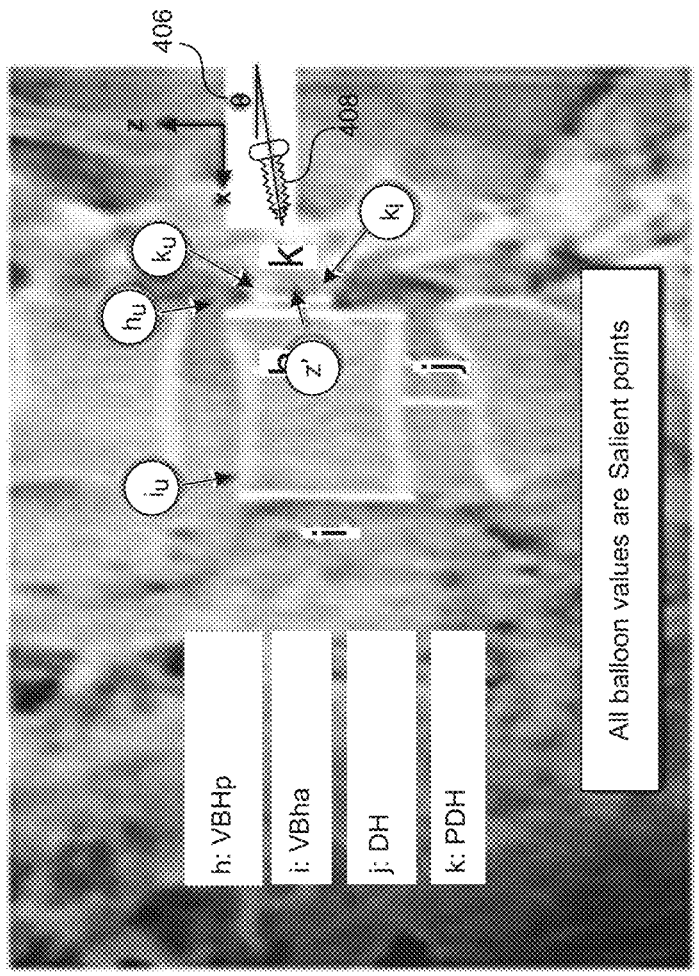
FIG. 4B illustrates computations for determining an XY angle for a spinal screw, according to an embodiment.

FIG. 4B illustrates computations for determining the XY angle ($\theta$) 406 using the salient points, according to an embodiment. It should be noted that positions of X and Y co-ordinates of the regions of interest may be determined based on a location of at least one salient feature present in the image. Further, FIG. 4A illustrates a position entry point 404 for the spinal screw, and FIG. 4B illustrates a position entry point 408 for the spinal screw. Upon determining, MRI data including the XY angle, the XZ angle, and the position entry point for the spinal screw, may be stored in the abnormalities module 110.

Post identification of the angels and the entry point for an implant, the system 102 may determine additional implant configuration features. For example, the system 102 can determine a maximum implant (e.g. spinal screw) diameter, a minimum implant diameter, and a length of the implant to be used during a spinal surgery. For example, upon determining the maximum spinal screw diameter and the length of the spinal screw, the procedure MRI data may be updated in the abnormalities module 110.

Figure 5:
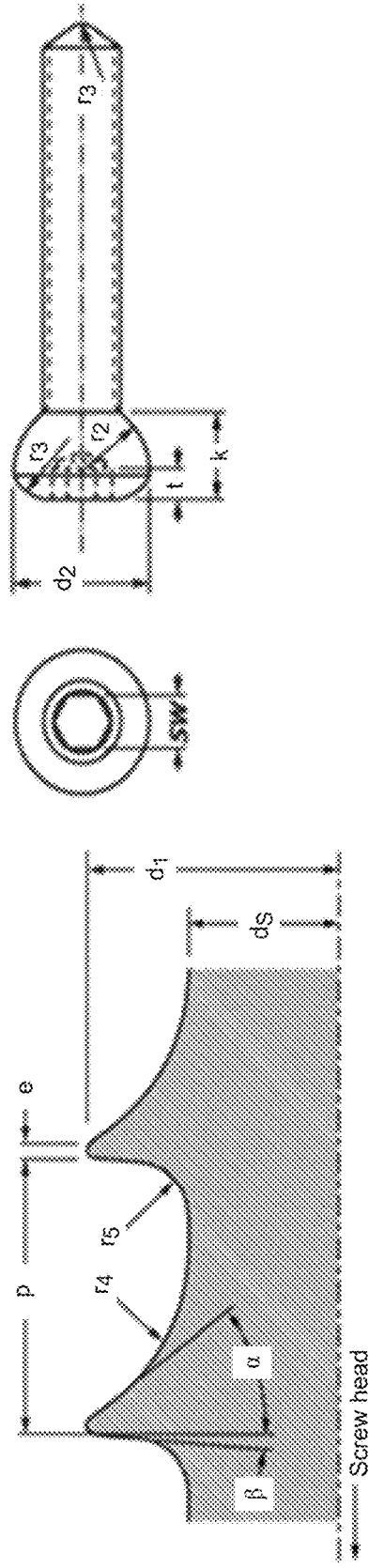
FIG. 5 illustrates a spinal screw and dimensions of the spinal screw, according to an embodiment.

In the spinal surgery example, the spinal screw having the determined maximum screw diameter and the length may be identified. The spinal screw may be suggested, to the surgeon, for usage during the spinal surgery. In one case, a spinal screw HA and dimensions of the spinal screw HA may be illustrated for the surgeon's selection, as shown in FIG. 5. As illustrated in FIG. 5, a schematic showing different parameters of the spinal screw HA, dimensions of the spinal screw HA, and a schematic of threads of the spinal screw HA are shown, according to an embodiment. Further, different such details related to spinal screws HB, spinal screws HD, and other known spinal screws may be presented to the surgeon for usage during the spinal surgery, thereby assisting the surgeon during the spinal surgery.

As another example, for an ACL replacement, upon determining the entry point and angle for a tibial tunnel for attaching a replacement graft, the system 102 can identify a depth for the tibial tunnel such that it will end above the center of the knee joint without piercing surrounding tissue. In addition, dimensions for the ACL graft itself and/or for screws or other fastening components can be suggested.

Figure 6:
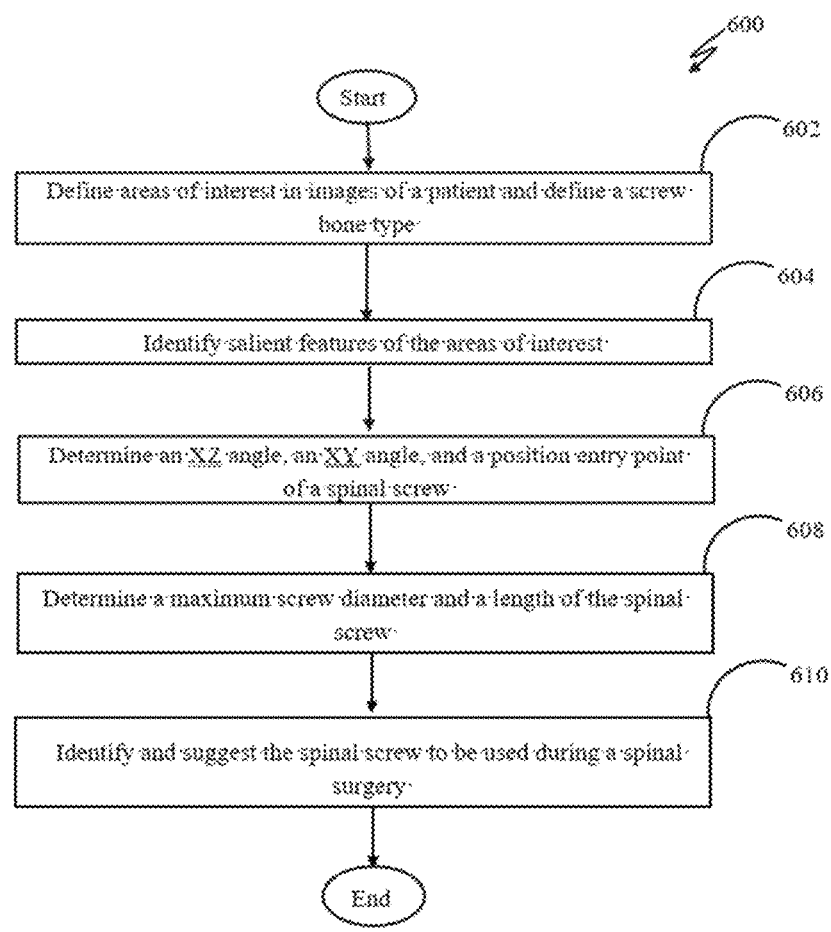
FIG. 6 illustrates a flowchart showing a method for providing assistance to the surgeon during the spinal surgery, according to an embodiment.

The flowchart 600 of FIG. 6 shows the architecture, functionality, and operation for providing assistance to a surgeon during a spinal surgery, according to an embodiment. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments. For example, two blocks shown in succession in FIG. 6 may in fact be executed substantially concurrently or the blocks may sometimes be executed in the reverse order, depending upon the functionality involved. Any process descriptions or blocks in flowcharts should be understood as representing modules, segments, or portions of code which include one or more executable instructions for implementing specific logical functions or steps in the process, and alternate implementations are included within the scope of the example embodiments in which functions may be executed out of order from that shown or discussed, including substantially concurrently or in reverse order, depending on the functionality involved. In addition, the process descriptions or blocks in flow charts should be understood as representing decisions made by a hardware structure such as a state machine. The flowchart 600 starts at step 602 and concludes at step 610.

At step 602, areas of interest may be defined in diagnostic data of a patient and a screw bone type may be defined, during a spinal surgery. The diagnostic data may include images of the patient. The images may be any of camera images, Magnetic Resonance Imaging (MRI) images, ultrasound images, Computerized Aided Tomography (CAT) scan images, Positron Emission Tomography (PET) images, and X-Ray images.

At step 604, salient features of areas of interest may be identified from the diagnostic data. In one case, the images may be analyzed to identify abnormalities and the salient features, for performing spinal surgeries on the patients.

At step 606, an XZ angle, an XY angle, and a position entry point for an implant (e.g. a spinal screw) are determined. In one case, the XZ angle, the XY angle, and the position entry point may be determined based on the salient features.

At step 608, a maximum screw diameter and a length of the screw to be used during the spinal surgery may be determined based on the XY angle, the XZ angle, and the position entry point of the screw. Upon determining the maximum screw diameter and the length of the screw, the procedure MRI data may be updated in an abnormalities module 110.

At step 610, the screw implant to be used during a surgery may be identified and suggested to a surgeon. The screw implant may be identified based on the maximum screw diameter and the length of the screw.

Figure 7:
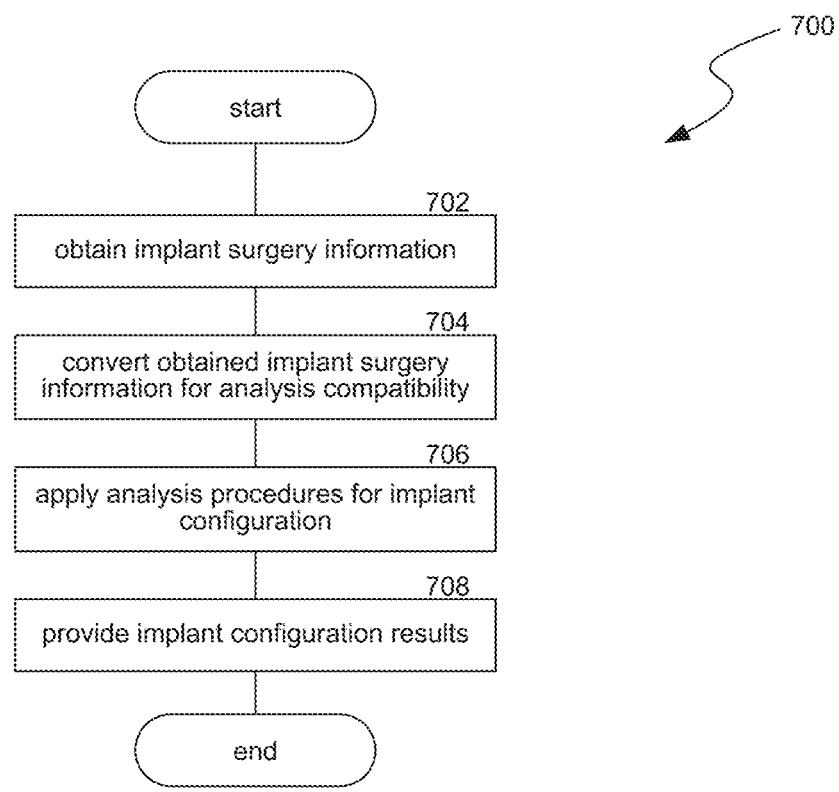
FIG. 7 illustrates a flowchart showing a method for generating implant configurations.

FIG. 7 illustrates a flowchart showing a method 700 for generating implant configurations. At block 702, method 700 can obtain implant surgery information such as images, patent history, circumstance, test results, biographic data, surgeon recommendations, implant specifics, etc. Implant surgery images can be of parts of a patient, such as camera images, Magnetic Resonance Imaging (MRI) images, ultrasound images, Computerized Aided Tomography (CAT) scan images, Positron Emission Tomography (PET) images, X-Ray images, 2D or 3D virtual models, CAD models, etc. Additional implant surgery information can include, e.g. sex, age, height, weight, type of pathology, occupation, activity level, implant types and dimensions, availability of available implants, or aspects of a surgeon's preoperative plan (e.g. surgeon's initial implant configuration, detection and measurement of the patient's anatomy on images, etc.)

The implant surgery information can be obtained in various manners such as through direct user input (e.g. through a terminal or by interacting with a web service), through automatic interfacing with networked databases (e.g. connecting to patient records stored by a hospital, laboratory, medical data repositories, etc.), by scanning documents, or through connected scanning, imaging, or other equipment. The patient data can be gathered with appropriate consent and safeguards to remain HIPPA compliant.

At block 704, method 700 can convert the implant surgery information obtained at block 702 to be compatible with analysis procedures. The conversion can depend on the analysis procedure that will be used. As discussed below in relation to block 706, analysis procedures can include directly applying a machine learning model, applying an algorithm with multiple stages where any of the stages can provide machine learning model predictions (see FIG. 8A), or applying a virtual modeling system (see FIG. 8B).

In some implementations, the conversion of the implant surgery information can include formatting the implant surgery information for entry to a machine learning model. For example, information such as patient sex, height, weight, etc. can be entered in a feature vector, such as a sparse vector with values corresponding to available patient characteristics. In some implementations, the conversions can include transforming images from the implant surgery information into a format suitable for input to a machine learning model, e.g. an array of integers representing pixels of the image, histograms, etc. In some implementations, the conversion can include identifying surgery target features (detection and measurement of the patient's anatomy on images), characterizing surgery targets, or modeling (i.e. creating a virtual model of) the implant surgery target. For example, in a spinal surgery, this can include measuring vertebrae features on an image, converting 2D images of vertebrae into a 3D model, or identifying which vertebrae from a series of images are to be the target of the implant operation. As another example, in an ACL replacement surgery, this can include identifying and measuring features in an image such as location, size, and spacing of anatomy such as of the femur, patella, remaining portion of meniscus, other ligaments, etc., converting 2D images of the knee into a 3D model, or identifying other areas of damage (e.g. fractures, torn cartilage, other ligament tears, etc.).

In various implementations, the conversion process can be automatic, human supervised, or performed by a human technician, e.g. using tools such as a digital ruler and a digital angle finder. Further in the spinal surgery example, the conversion can include identifying a target set of vertebrae, initially localizing and marking the target set of vertebrae, performing segmentation for each of the target set of vertebrae, and marking cortical boundaries. In some implementations, input for the spinal implant surgery can specify a target set of vertebrae, however the surgical assistance system 164 can automatically perform calculations for additional vertebrae that weren't specified in the inputs. This can give the surgeon an option to expand the set of vertebrae to be fused, either prior to the operation or even during the procedure. In the ACL replacement surgery example, the conversion can include identifying a graft type (e.g. patella tendon, hamstring, cadaver ACL, etc.), initially localizing or marking the target drilling sites, performing segmentation for the target features (e.g. end of the femur), and marking boundaries (e.g. bone edges, meniscus edges, synovial membrane, etc.).

At block 706, method 700 can apply analysis procedures, using the converted implant surgery information from block 704, to identify implant configuration(s). In various implementations, the analysis procedures can include directly applying a machine learning model, applying a sequence of steps that can include one or more machine learning models, and/or generating a virtual model of the surgery target area and applying heuristics for implant configuration selection.

To apply a machine learning model directly, method 700 can provide the converted implant information to a machine learning model trained to specify implant configurations. A machine learning model can be trained to take input such as representations of a series of images and a feature vector for the patient and other aspects of the surgery (e.g. implant availability, surgeon specialties or ability indicators, equipment available, etc.) and can produce results that implant configurations. For example, for a spinal surgery, the machine learning model can suggest pedicle screw configurations, e.g. characteristics such as screw diameter, length, threading and application parameters such as screw insertion point, angle, rotation speed, etc. As another example, for an ACL replacement surgery, the machine learning model can suggest graft type, attachment type (e.g. screw material, length, or configuration features), graft attachment locations, drill depths, etc.

In some implementations, the converted implant information can be used in a multi-stage process for selecting aspects of an implant configuration. For example, for a spinal surgery, the multi-stage process can include method 800 or method 850, discussed below. In various steps of this these processes, either an algorithm can be used to generate results for that step or a machine learning model, trained for that step, can be applied.

In some implementations, the procedure for identifying implant configurations for a spinal surgery can include processing implant surgery information to locate targeted vertebrae and their pedicles in images, on available axes; identifying and tagging vertebrae characteristics; determining a preferred screw insertion point based on a mapping between tags and insertion point criteria (e.g. where the mapping can be a representation of a medical definition of a pedicle screw insertion point—described below); performing measurements, on the images, of the pedicle isthmus width and height and length of the pedicle and vertebral body, starting at the preferred insertion point; measuring the angle between the line used to determine length and the sagittal plane, in the axial view; and measuring the angle between that length line and the axial plane.

In some implementations, machine learning models can be trained to perform some of these tasks for identifying implant configurations. For example, machine learning models can be trained to identify particular vertebral pedicles in various images, which can then be atomically measured and aggregated across images, e.g. storing minimal, maximal, median, or average values, as appropriate given the target being measured. As another example, a machine learning model can receive the set of images and determine an order or can select a subset of the images, for automatic or manual processing. In some implementations, a machine learning model can be used to localize and classify the target within an image, such as by identifying a target vertebra or localizing the end of the femur or meniscus edges. In some implementations, a machine learning model can be used to segment target vertebrae, femur, tibia, or other anatomical features in the target area, to determine their boundaries. In some implementations, a machine learning model can be used to localize insertion points. In some implementations, a machine learning model can be used to segment images to determine boundaries of anatomical structures (e.g., boundaries of bones, organs, vessels, etc.), density of tissue, characteristics of tissue, or the like.

In various implementations, the results from the above stages can be used in inference formulae to compute the implant configurations. For example, a maximal screw diameter can be determined using the smallest pedicle isthmus dimension found across all the images of the target vertebrae (which can be adjusted to include a safety buffer). As another example, a maximal screw length can be determined using the smallest measurement of pedicle and vertebral body length, across all the target vertebra in question (which can be adjusted to include a safety buffer).

Machine learning models, as used herein, can be of various types, such as Convolutional Neural Networks (CNNs), other types of neural networks (e.g. fully connected), decision trees, forests of classification trees, Support Vector Machines, etc. Machine learning models can be trained to produce particular types of results, as discussed below in relation to FIG. 9. For example, a training procedure can include obtaining suitable training items with input associated with a result, applying each training item to the model, and updating model parameters based on comparison of model result to training item result.

In some implementations, automated selection of implant configurations can be limited to only cases likely to produce good results, e.g. only for certain pathologies, types of patients, surgery targets (e.g. the part of the spine that needs to be fused), or where confidence scores associated with machine learning model outputs are above a threshold. For example, in the spinal surgery example, automation can be limited to common types of spinal fusions, such as L3/L4, L4/L5, or L5/S1, certain pathologies such as spondylolisthesis or trauma, or patients with certain characteristics, such as being in a certain age group. As another example, for an ACL replacement, automation can be limited to cases without other ligament tears.

At block 708, method 700 can provide results specifying one or more features of an implant configuration. For example, the results for a spinal surgery can include selection of pedicle screw type and dimensions for each vertebra and guidance on an insertion point and angle for each screw. As another example, results for an ACL replacement surgery can include selection of implant graft type, connection type, joint dimensions, and guidance on connection points such as drill locations and depths. In some implementations, the results can be specified in a natural language, e.g. using templates that can be filled in with recommendations. In some cases, the results from the analysis of block 706 can be mapped to particular reasons for the implant configuration recommendations, and these reasons can be supplied along with the recommendations.

In some implementations, the results can be based on medical definitions of preferred implant configurations, where the preferred implant configurations can be mapped to a particular surgical target area based on the results from block 706. For example, results for spinal surgery pedicle screws can include a preferred insertion point, e.g. defined, for lumbar vertebrae, at the intersection of the superior articular facet, transverse process, and pars interarticularis; and for thoracic spine or cervical spine, at the intersection of the superior articular facet plane and transverse process. As another example, a preferred screw angle can be, in axial view, the angle between the sagittal plane and the line defined by the insertion point and midpoint of the pedicle isthmus. In sagittal view the preferred screw angle can be parallel to the superior vertebral endplate. In addition, a maximal screw length can be defined as the distance between the insertion point and the far cortical boundary of the vertebra, at a particular screw angle. A maximal screw diameter can be the minimal width of the pedicle isthmus, on any axis. Each of these can be modified to include a certain safety buffer, which can vary depending on the size of the vertebra. The results from block 706 can identify features of an individual patient, which can be used in conjunction with the foregoing implant configuration definitions to specify patient specific implant configurations, e.g. in natural language, as image annotations, in a 3D model, as discussed below.

The implant configuration results can be specified in various formats. For example, results can be in a natural language, coordinates one of various coordinate systems, as instructions for a robotic system, as annotations to one or more images, or as a virtual model of the surgery target area. The results can be used to augment the implant surgery in multiple ways. For example, results can be added to a preoperative plan. Results can trigger acquisition of implant materials, such as by having selected implants ordered automatically or having designs for patient-specific screws provided for 3D-printing. As another example, results can be used to provide recommendations during a surgical procedure, e.g. with text or visual annotations provided as overlies on a flat panel display, through auditory or haptic feedback alerts, or using an AR or VR system, e.g. to display an overlay of the implant on the patient anatomy or to display guidance on the suggested insertion point and angle. In some implementations, the results can be used to control robotic systems, e.g. causing a robotic arm to align itself according to the recommended insertion point and angle, which may be first confirmed by a surgeon.

The method 700 can be used in a wide range of procedures, e.g. open procedures, minimally invasive procedures, orthopedic procedures, neurological procedures, reconstructive implants, maxillofacial procedures (e.g., maxillary implants), or other procedure. In some surgical procedures, the implant information at block 702 can include implant dimensions, material information (e.g., composition of implant), and images of the patient. At block 706, the implant configuration can be implant dimensions (e.g., when in a delivery state or implanted state), implant functionality, or the like.

Figure 8A:
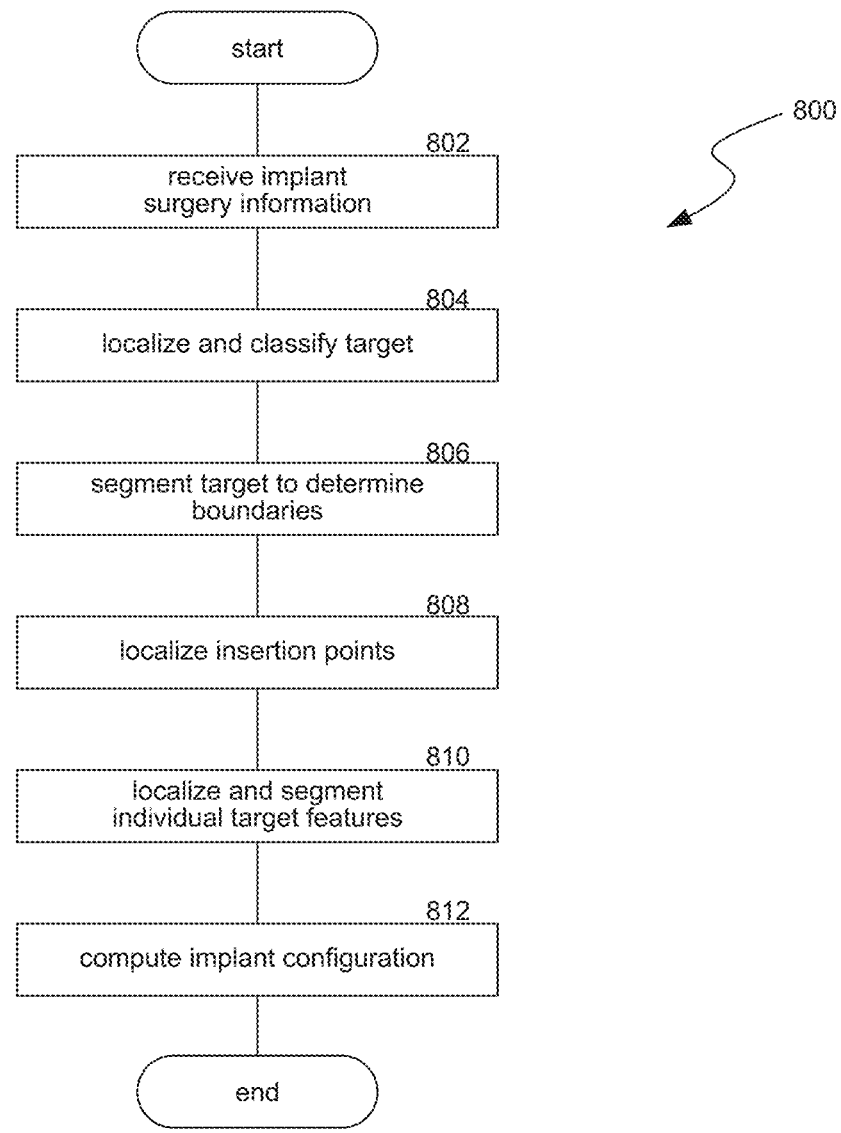
FIG. 8A illustrates a flowchart showing a method for applying analysis procedures that can utilize machine learning models, according to an embodiment.

FIG. 8A illustrates a flowchart showing a method 800 for applying analysis procedures that can utilize machine learning models, according to an embodiment. In some implementations, method 800 is performed as a sub-process of block 706. At block 802, method 800 can receive implant surgery information. This can be some of the converted implant surgery information from block 704. In some implementations, the implant surgery information can include one or more images of the surgery target area, e.g. MRI scans of a spine, X-rays of a wrist, ultrasound images of an abdomen, etc.

At block 804, method 800 can localize and classify a target in one or more of the images of the surgery target area. In various implementations, this can be accomplished by applying a machine learning model trained for the particular target area to identify surgical targets or by finding a centroid point of each displayed vertebra, performing vertebral classification using image recognition algorithms, and determining whether the classified vertebrae match a list of vertebrae identified for the surgery. In some implementations, if the image does not contain at least one target of interest, the image can be disregarded from further processing.

At block 806, method 800 can segment the identified target(s) from block 804 to determine their boundaries. At block 808, method 800 can localize implant insertion points. In some implementations, blocks 806 and 808 can be performed using machine learning models or algorithms, e.g. that identify particular patterns, changes in color, shapes, etc.

At block 810, method 800 can localize and segment individual target features. For example, in a spinal surgery where targets are vertebrae, at block 810 method 800 can identify vertebrae pedicles and their isthmus, and measure these features. In some implementations, this can be accomplished using a machine learning model trained to detect each type of feature. In some implementations, detecting the pedicle and the isthmus of vertebra from annotated images can include measuring the isthmus width and tracking the minimal value across images and planes, defining the angle between the line that passes through at least two midpoints in the pedicle, and the reference plane, measuring the maximal length through that line, and tracking the minimal value across measurements. In some implementations, isthmus determination and measurement can be accomplished by starting at a point inside a pedicle, computing the distance to pedicle borders in multiple directions, taking the minimum length. In other implementations, the isthmus determination and measurement can be accomplished by scanning, for example using horizontal lines that intersect with pedicle borders in an axial view, and finding the minimum-length line.

In some implementations, the steps performed at any of blocks 804-810 can be repeated for each of multiple target area images, aggregating results from the multiple images. For example, in a step for identifying and measuring vertebrae pedicles, an aggregated measurement for a particular pedicle can be the minimum measured width of the pedicle from all of the images showing that particular pedicle.

At block 812, method 800 can use results from any of blocks 804-810 to compute an implant configuration (e.g. characteristics and application parameters). For example, the minimum width of a pedicle found across the images showing that pedicle, with some buffer added, can be the selected width characteristic of a pedicle screw implant. As another example, a screw angle could be determined using an identified insertion point and a center of the pedicle isthmus, with respect to center axis, depending on the image plane. The angles in axial and sagittal planes can be either the median or average angles across the multiple images. As a further example, a maximal screw length can be determined as the length of the line defined by the insertion point, the insertion angle, and the point where the line hits the cortical wall of the vertebra, minus some safety buffer. This length can be computed from multiple images and the minimum across all the images can be used for of this screw.

Figure 8B:
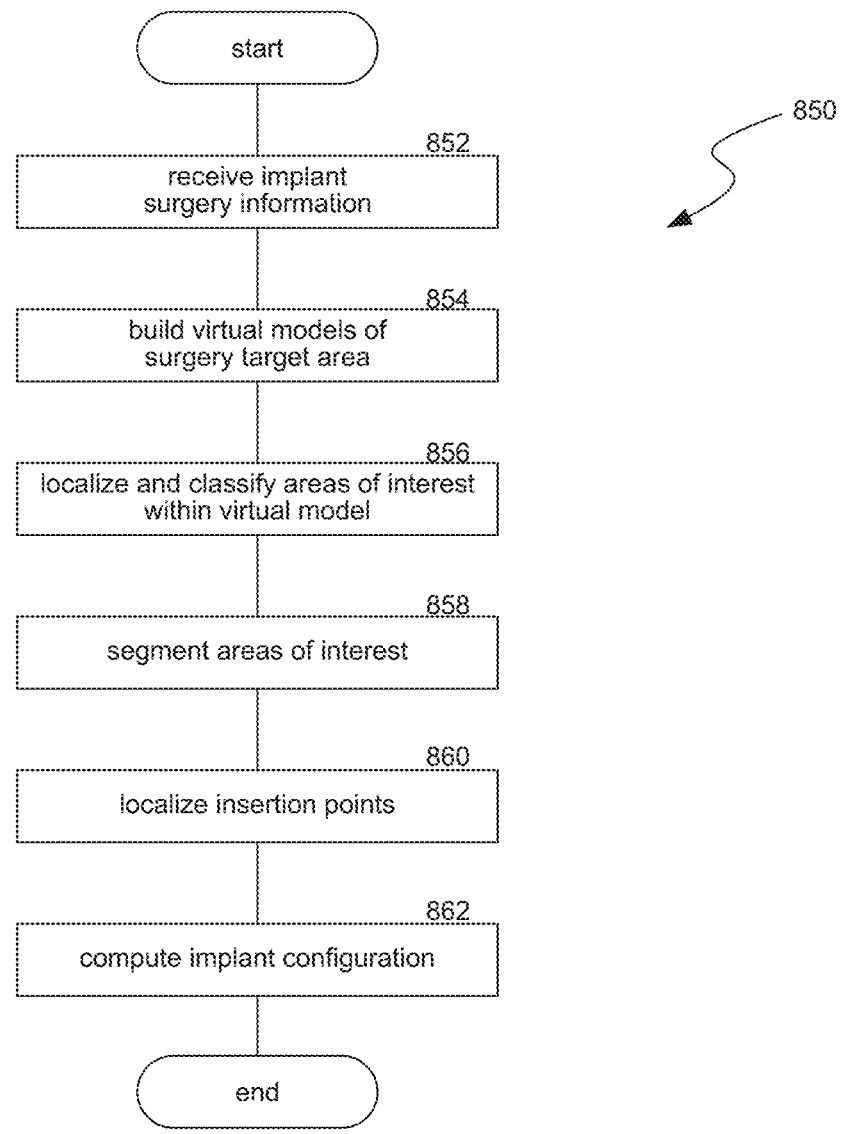
FIG. 8B illustrates a flowchart showing a method for applying analysis procedures that can utilize virtual models, according to an embodiment.

FIG. 8B illustrates a flowchart showing a method 850 for applying analysis procedures that can utilize virtual models, according to an embodiment. In some implementations, method 850 is performed as a sub-process of block 706. At block 852, method 850 can receive implant surgery information. This can be some of the converted implant surgery information from block 704. In some implementations, the implant surgery information can include one or more images of the surgery target area.

At block 854, method 850 can build one or more virtual models of the target surgery area based on the images and/or other measurement data in the implant surgery information. A virtual model, as used herein, is a computerized representation of physical objects, such as the target area of a surgery (e.g. portions of a patient's spine) and/or implants (e.g. screws, rods, etc.). In some implementations, virtual models can be operated according to known physical properties, e.g. reactions to forces can be predicted according to known causal relationships. In various implementations, the virtual models generated by method 850 can be two-dimensional models or three-dimensional models. For example, a two-dimensional model can be generated by identifying portions of an image as corresponding to parts of a patient's anatomy, such that a computing system can determine how implant characteristics would fit in relation to the determined anatomy parts. As another example, a three-dimensional model can be generated by identifying shapes and features in individual images, from a set of successive images, and mapping the identified shapes and features into a virtual three-dimensional space, using relationships between images. Finite element analysis techniques can be used to predict stresses, strains, pressures, facture, and other information and be used to design implants, surgical tools, surgical techniques, etc. For example, the implant configuration can be determined based on predetermined stresses (e.g., maximum allowable stresses in the tissue and/or implant, yield strength of anatomical structures and/or implant components, etc.), fracture mechanics, or other criteria defined by the physician or automatically determined based on, for example, tissue characteristics, implant design, or the like. In some embodiments, fatigue life can be predicted using stress or strain based techniques.

A virtual model can also analyze mechanical interaction between a patient's vertebrae, loading of implants, and other devices (e.g., rods, ties, brackets, plates, etc.) coupled to those implants. The output of these analyses can be used to select pedicle screw configurations, insertion trajectories, and placement location to optimize screw pull-out strength, maximum allowable loading (e.g., axial loads, shear loads, moments, etc.) to manage stresses between adjacent vertebrae, or maximum allowable stress in regions of the bone at risk for fracture.

In some embodiments, a user could identify areas of weakened bone or areas on images of the patient where there is risk of a fracture due to the presence of a screw or other implant. This information can be provided to the virtual model. The virtual model can be used to evaluate whether the configuration or location of the implant would create an unacceptable risk of fracture in the identified region. If so, the system could alert the user to that risk or modify the implant configuration or the procedure to reduce the risk to an acceptable level. In other embodiments, the system could identify these areas of high fracture risk automatically. In yet another embodiment, the system could provide data to the user such as the maximum torque to apply to a given pedicle screw during the surgical procedure such that tissue trauma, risk of fracture, or adverse advents is minimized.

At block 856, method 850 can localize and classify areas of interest within the virtual model(s) from block 854. This can be accomplished using object recognition that matches shapes of known objects to shapes within the virtual models. For example, in a virtual model for a spinal surgery, the images can be MRI images of vertebrae. The virtual vertebrae can be labeled (e.g. c1-s5) and virtual model vertebrae corresponding to the vertebrae for which the spinal procedure is planned can be selected as the areas of interest. In some implementations, additional areas around the selected areas can be added to the areas of interest, allowing the surgeon to select alternative options before or during the procedure. For example, the one or two vertebrae adjacent, on one or both sides, to the planned vertebrae can be additionally selected.

At block 858, method 850 can segment the areas of interest, identified at block 856, to determine various boundaries and other features, such as the pedicle boundaries and the pedicle isthmus. In some implementations, the segmentation or boundary determinations can be performed using a machine learning model. The machine learning model can be trained, for the type of implant surgery to be performed, to receive a portion of a virtual model and identify target portion segmentations or boundaries.

At block 860, method 850 can localize an insertion point for the implant in the target area. In some implementations, this can be accomplished by applying a machine learning model trained to identify insertion points. In some implementations, localizing insertion points can be accomplish using an algorithm, e.g. that identify particular patterns, changes in color, shapes, etc. identified as corresponding to preferred implant insertion points.

At block 862, method 850 can compute an implant configuration based on the virtual model(s) and/or determinations made in blocks 856-860. In some implementations, the implant can be associated with requirements for their application and properties to maximize or minimize. In these cases, the implant configuration can be specified as the configuration that fits with the virtual model, achieving all the requirements, and optimizing the maximizable or minimizable properties. For example, when method 850 is performed to determine pedicle screw configurations for a spinal surgery, virtual pedicle screws can be placed in a virtual model generated at block 854, according to the insertion points determined at block 860. The virtual pedicle screws can further be placed to: not breach cortical vertebral boundaries (e.g. determined at block 858), with a specified amount of buffer, while maximizing the screw diameter and length, taking into consideration required buffers and close to optimal insertion angle, defined by the pedicle isthmus center and insertion point, for each vertebra (e.g. determined at block 858). In some implementations, this placement of the implant can be performed as a constraint optimization problem. For example, a virtual screw can be placed inside the segmented vertebral body in the virtual model. The placement can then be adjusted until an equilibrium is reached that optimizes the parameters while conforming to the implant constraints. For example, method 850 can maximizing screw diameter and length while aligning with an optimal angle and avoiding cortical breaches.

Figure 9:
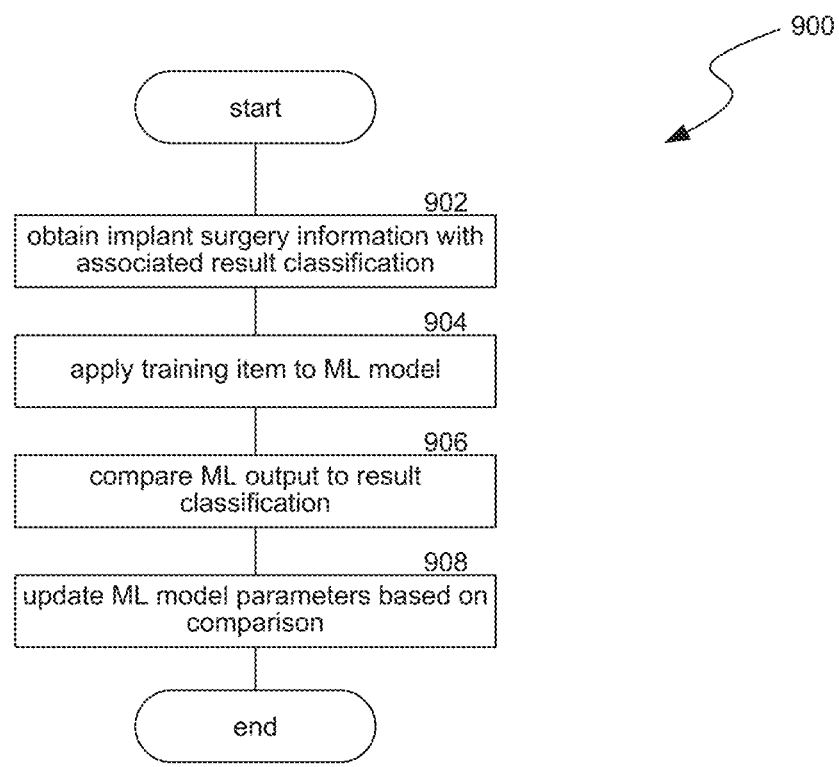
FIG. 9 illustrates a flowchart showing a method for training a machine learning model, according to an embodiment.

FIG. 9 illustrates a flowchart showing a method for training a machine learning model, according to an embodiment. Machine learning models, such as neural networks, can be trained to produce types of results. A neural network can be trained by obtaining, at block 902, a quantity of "training items," where each training item includes input similar to input the model will receive when in use and a corresponding scored result. At block 904, the input from each training item can be supplied to the model to produce a result. At block 906, the result can be compared to the scored result. At block 908, model parameters can then be updated, based on how similar the model result is to the scored result and/or whether the score is positive or negative.

For example, a model can be trained using sets of preoperative MRI scans of vertebrae paired with pedicle screw placements used in the surgery and corresponding scores for the result of that surgery. The images can be converted to arrays of integers that, when provided to the machine learning model, produce values that specify screw placements. The screw placements can be compared to the actual screw placement used in the surgery that produced the training item. The model parameters can then be adjusted so the model output is more like the screw placement used in the surgery if the surgery was a success or less like the screw placement used in the surgery if the surgery was a failure. The amount of adjustment to the model parameters can be a function of how different the model prediction was from the actual screw configuration used and/or the level of success or failure of the surgery.

As discussed above, machine learning models for the surgical assistance system can be trained to produce various results such as: to directly produce implant configurations upon receiving implant surgery information, to identify particular vertebral pedicles in various images, to determine an order or subset of images for processing, to localize and classify the target within an image, to segment target vertebrae, to determine boundaries or other features, to localize insertion points, etc.

In various implementations, the training data for a machine learning model can include input data such as medical imaging data, other patient data, or surgeon data. For example, model input can include images of the patient, patient sex, age, height, weight, type of pathology, occupation, activity level, etc., specifics of implant systems (e.g. types and dimensions), availability of available implants, or aspects of a surgeon's preoperative plan (e.g. surgeon's initial implant configuration, detection and measurement of the patient's anatomy on images, etc.) In some implementations, model training data input can include surgeon specifics, such as statistics or preferences for implant configurations used by the surgeon performing the implant surgery or outcomes for implant usages. For example, surgeons may have better skill or experience with particular implant configurations, and the system can be trained to select implant configurations the particular surgeon is more likely to use successfully. The training data input can be paired with results to create training items. The results can be, for example, human annotated medical imaging data (as a comparison for identifications such as boundaries and insertion points identified by a model), human feedback to model outputs, surgeons' post-operative suggestion feedback (e.g. whether the surgeon accepted model provided recommendations completely, or made certain changes, or disregarded), surgeons post-operative operation outcome success score, post-operative images that can be analyzed to determine results, the existence of certain positive or negative patient results, such as cortical breaches or other complications that might have occurred in the procedure, overall level of recovery, or recovery time.

In an illustrative embodiment, any of the operations, processes, etc. described herein can be implemented as computer-readable instructions stored on a computer-readable medium. The computer-readable instructions can be executed by a processor of a mobile unit, a network element, and/or any other computing device.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a CD, a DVD, a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components. All applications and patents referenced herein are incorporated by reference in their entireties.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting.

What is claimed is:

1. A computer-implemented method for providing a patient-specific implant for a patient, the method comprising:
   transmitting, from at least one user device, one or more criteria associated with a virtual anatomical model of a portion of a patient, wherein the virtual anatomical model is based on one or more images of the patient, and the virtual anatomical model is viewable via the at least one user device for evaluating a surgical procedure using the patient-specific implant;
   receiving a notification indicating that at least one of the one or more criteria is unacceptable;
   transmitting, from the at least one user device, an alternative option from the user for the at least one unacceptable criteria;
   displaying, via the at least one user device, a modified virtual anatomical model of the patient's spine based on the alternative option from the user; and
   transmitting, from the at least one user device, user approval of the modified anatomical model of the patient's spine so that a remote computing system designs the patient-specific implant that fits the modified virtual anatomical model of the patient's spine.

2. The computer-implemented method of claim 1, further comprising displaying at least one anatomical analytic for the patient's spine based on the modified virtual anatomical model of the patient's spine, wherein displaying the modified virtual anatomical model includes displaying at least one annotated image of the modified virtual anatomical model.

3. The computer-implemented method of claim 1, further comprising receiving virtual implantation simulation data of the surgical procedure for implanting the patient-specific implant based on the modified virtual anatomical model.

4. The computer-implemented method of claim 1, wherein displaying the modified virtual anatomical model is performed by displaying one or more annotated images of the modified virtual anatomical model of the patient's spine for review by the user, wherein the one or more annotated images includes at least one measurement between anatomical features of the patient's spine.

5. The computer-implemented method of claim 1, further comprising displaying annotated anatomical images associated with the patient's spine, wherein the one or more criteria include implant design criteria.

6. The computer-implemented method of claim 1, further comprising receiving, from a spine network of the remote computing system, abnormality analytics quantifying one or more anatomical features of the patient.

7. The computer-implemented method of claim 1, wherein the one or more criteria includes at least one of a target measurement for a target outcome of the patient's spine and a characteristic of an anatomical feature of the patient's spine.

8. A computing system comprising:
one or more processors; and
one or more memories storing instructions that, when executed by the one or more processors, cause the computing system to perform a process comprising:
transmitting, from at least one user device, one or more criteria associated with a virtual anatomical model of a portion of a patient, wherein the virtual anatomical model is based on one or more images of the patient, and the virtual anatomical model is viewable via the at least one user device for evaluating a surgical procedure using the patient-specific implant;
receiving a notification indicating that at least one of the one or more criteria is unacceptable;
transmitting, from the at least one user device, an alternative option from the user for the at least one unacceptable criteria;
displaying, via the at least one user device, a modified virtual anatomical model of the patient's spine based on the alternative option from the user; and
transmitting, from the at least one user device, user approval of the modified anatomical model of the patient's spine so that a remote computing system designs the patient-specific implant that fits the modified virtual anatomical model of the patient's spine.

9. The computing system of claim 8, wherein the process further comprises displaying at least one image of the modified virtual anatomical model and at least one anatomical analytic for the patient's spine based on the modified virtual anatomical model of the patient's spine.

10. The computing system of claim 8, wherein the process further comprises receiving virtual implantation simulation data for the patient-specific implant using the modified virtual anatomical model.

11. The computing system of claim 8, wherein displaying the modified virtual anatomical model is performed by displaying one or more annotated images of the modified virtual anatomical model of the patient's spine for review by the user, wherein the one or more annotated images includes at least one measurement between anatomical features of the patient's spine.

12. The computing system of claim 8, wherein the process further comprises displaying annotated anatomical images associated with one or more images of a surgical target area.

13. The computing system of claim 8, wherein the process further comprises receiving, from a spine network of the remote computing system, abnormality analytics quantifying anatomical features of the patient.

14. The computing system of claim 8, wherein the one or more criteria includes at least one of a target measurement for a target outcome of the patient's spine and a characteristic of an anatomical feature of the patient's spine.

15. A non-transitory computer-readable storage medium storing instructions that, when executed by a computing system, cause the computing system to perform a process comprising:
transmitting, from at least one user device, one or more criteria associated with a virtual anatomical model of a portion of a patient, wherein the virtual anatomical model is based on one or more images of the patient, and the virtual anatomical model is viewable via the at least one user device for evaluating a surgical procedure for a patient-specific implant;
receiving a notification indicating that at least one of the one or more criteria is unacceptable;
transmitting, from the at least one user device, an alternative option from the user for the at least one unacceptable criteria;
displaying, via the at least one user device, a modified virtual anatomical model of the patient's spine based on the alternative option from the user; and
transmitting, from the at least one user device, user approval of the modified anatomical model of the patient's spine so that a remote computing system designs the patient-specific implant that fits the modified virtual anatomical model of the patient's spine.

16. The non-transitory computer-readable storage medium of claim 15, wherein the process further comprises displaying at least one image of the modified virtual anatomical model and at least one anatomical analytic for the patient's spine based on the modified virtual anatomical model of the patient's spine.

17. The non-transitory computer-readable storage medium of claim 15, wherein the process further comprises displaying one or more values for the patient's spine based on the virtual model of the patient's spine, wherein the one or more values indicate a configuration for the patient's spine.

18. The non-transitory computer-readable storage medium of claim 15, wherein the process further comprises receiving virtual implantation simulation data for the patient-specific implant using the modified virtual anatomical model.

19. The non-transitory computer-readable storage medium of claim 15, wherein displaying the modified virtual anatomical model is performed by displaying one or more annotated images of the modified virtual anatomical model of the patient's spine for review by the user, wherein the one or more annotated images includes at least one measurement between anatomical features of the patient's spine.

20. The non-transitory computer-readable storage medium of claim 15, wherein the process further comprises: displaying annotated images associated with the one or more images or virtual model of a surgical target area.

21. A digital personalized surgical plan for designing a patient-specific implant for an anatomical outcome, wherein the digital personalized surgical plan is displayable via an electronic screen of at least one user device to provide viewing of a modified virtual anatomical model of at least a portion of a patient's body illustrating the anatomical outcome, wherein the at least one user device is configured to receive one or more criteria from a user and to receive approval of the digital personalized surgical plan, and wherein the digital personalized surgical plan is made by a process comprising:

transmitting, from at least one user device, one or more criteria associated with a virtual anatomical model of a portion of a patient, wherein the virtual anatomical model is based on one or more images of the patient, and the virtual anatomical model is viewable via the at least one user device for evaluating a surgical procedure with the patient-specific implant;

receiving a notification indicating that at least one of the one or more criteria is unacceptable;

transmitting, from the at least one user device, an alternative option from the user for the at least one unacceptable criteria;

displaying, via the at least one user device, a modified virtual anatomical model of the patient's spine based on the alternative option from the user; and transmitting, from the at least one user device, user approval of the modified anatomical model of the patient's spine so that a remote computing system designs the patient-specific implant that fits the modified virtual anatomical model of the patient's spine.

22. The digital surgical plan of claim 21, wherein the digital personalized surgical plan further includes one or more values for the patient's spine based on the at least one of a virtual anatomical model or a modified virtual three-dimensional model, wherein the one or more values indicate a configuration for the patient's spine.

\* \* \* \* \*